US012748921B2

(12) United States Patent
Price

(10) Patent No.: US 12,748,921 B2
(45) Date of Patent: Sep. 29, 2026

(54) READMISSION MODEL BASED ON SOCIAL DETERMINANTS OF HEALTH

(71) Applicant: MatrixCare, Inc., Bloomington, MN (US)

(72) Inventor: Robert W. Price, Lockport, IL (US)

(73) Assignee: MatrixCare, Inc., Bloomington, MN (US)

(*) Notice: Subject to any disclaimer, the term of this patent is extended or adjusted under 35 U.S.C. 154(b) by 198 days.

(21) Appl. No.: 18/193,420

(22) Filed: Mar. 30, 2023

(65) Prior Publication Data

US 2023/0315989 A1 Oct. 5, 2023

Related U.S. Application Data

(60) Provisional application No. 63/325,949, filed on Mar. 31, 2022.

(51) Int. Cl.

| | |
|---|---|
| ***G06F 40/284*** | (2020.01) |
| ***G06F 40/205*** | (2020.01) |
| ***G16H 10/60*** | (2018.01) |
| ***G16H 40/20*** | (2018.01) |
| ***G16H 50/20*** | (2018.01) |
| ***G16H 50/70*** | (2018.01) |

(52) U.S. Cl.

CPC .......... *G06F 40/284* (2020.01); *G06F 40/205* (2020.01); *G16H 10/60* (2018.01); *G16H 40/20* (2018.01); *G16H 50/20* (2018.01); *G16H 50/70* (2018.01)

(58) Field of Classification Search

CPC ...... G06F 40/284; G06F 40/205; G06F 40/30; G06F 40/216; G16H 10/60; G16H 40/20; G16H 50/20; G16H 50/70; G16H 50/30

See application file for complete search history.

(56) References Cited

U.S. PATENT DOCUMENTS

| | | | | |
|---|---|---|---|---|
| 12,205,695 B1 * | 1/2025 | Devaraja | ................ | G16H 10/20 |
| 2014/0095201 A1 * | 4/2014 | Farooq | .................. | G16H 50/30 705/3 |
| 2015/0227710 A1 * | 8/2015 | Pappada | ................ | G16H 70/20 705/2 |
| 2016/0125159 A1 * | 5/2016 | Ling | ...................... | G16H 40/20 705/3 |
| 2018/0052967 A1 * | 2/2018 | Boomershine | ......... | G16H 20/00 |
| 2020/0402665 A1 * | 12/2020 | Zhang | .................... | G16H 50/30 |
| 2020/0411193 A1 * | 12/2020 | Wald | ........................ | G06N 5/01 |
| 2021/0174968 A1 * | 6/2021 | Butterfield | .......... | G06F 18/2135 |
| 2023/0112369 A1 * | 4/2023 | Chopra | .................. | G06N 3/044 705/304 |
| 2023/0307136 A1 * | 9/2023 | Tsang | ..................... | G16H 50/70 |
| 2024/0153639 A1 * | 5/2024 | Elidan | .................... | G16H 50/70 |

* cited by examiner

*Primary Examiner* — Stella L. Woo

(74) *Attorney, Agent, or Firm* — Patterson + Sheridan, LLP

(57) ABSTRACT

Techniques to determine readmission risk profiles of patients admitted to a healthcare facility. A patient record for a patient admitted to the healthcare facility is received. The patient record includes social information determined for the patient. A machine learning model is applied to the patient record to determine a readmission risk profile of the patient. An indication of the readmission risk profile of the patient is output.

20 Claims, 19 Drawing Sheets

150

READMISSION MODEL BASED ON SOCIAL DETERMINANTS OF HEALTH

CROSS-REFERENCE TO RELATED APPLICATIONS

This application claims priority to U.S. Provisional Patent Application No. 63/325,949, filed Mar. 31, 2022, the entire content of which is incorporated herein by reference in its entirety.

BACKGROUND

Field

Embodiments in the present disclosure relate to determining a readmission risk profile of a patient by applying a machine learning model to social determinants of health.

Description of the Related Art

Healthcare has become an increasingly demanding field over the years. As the number of patients increases and as the needs of these patients increase, so do the demand and pressure placed on healthcare facilities. Despite earnest efforts, a number of patients are faced with readmission only shortly after being discharged from a healthcare facility. Failure to contain the readmission rate to manageable levels can adversely impact not just the quality of care delivered to patients but patient outcomes and the reputation of the healthcare facility itself.

SUMMARY

Embodiments presented in this disclosure provide a method, a non-transitory computer-readable medium, and a system to perform an operation for readmission risk modeling. The non-transitory computer-readable medium contains executable instructions. The system includes one or more computer processors and a memory containing an executable program executable by the one or more computer processors. The operation includes receiving a patient record for a patient admitted to a healthcare facility. The patient record includes social information determined for the patient. The operation also includes applying a machine learning model to the patient record to predict a readmission risk profile of the patient. The operation further includes outputting an indication of the readmission risk profile of the patient.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1A:
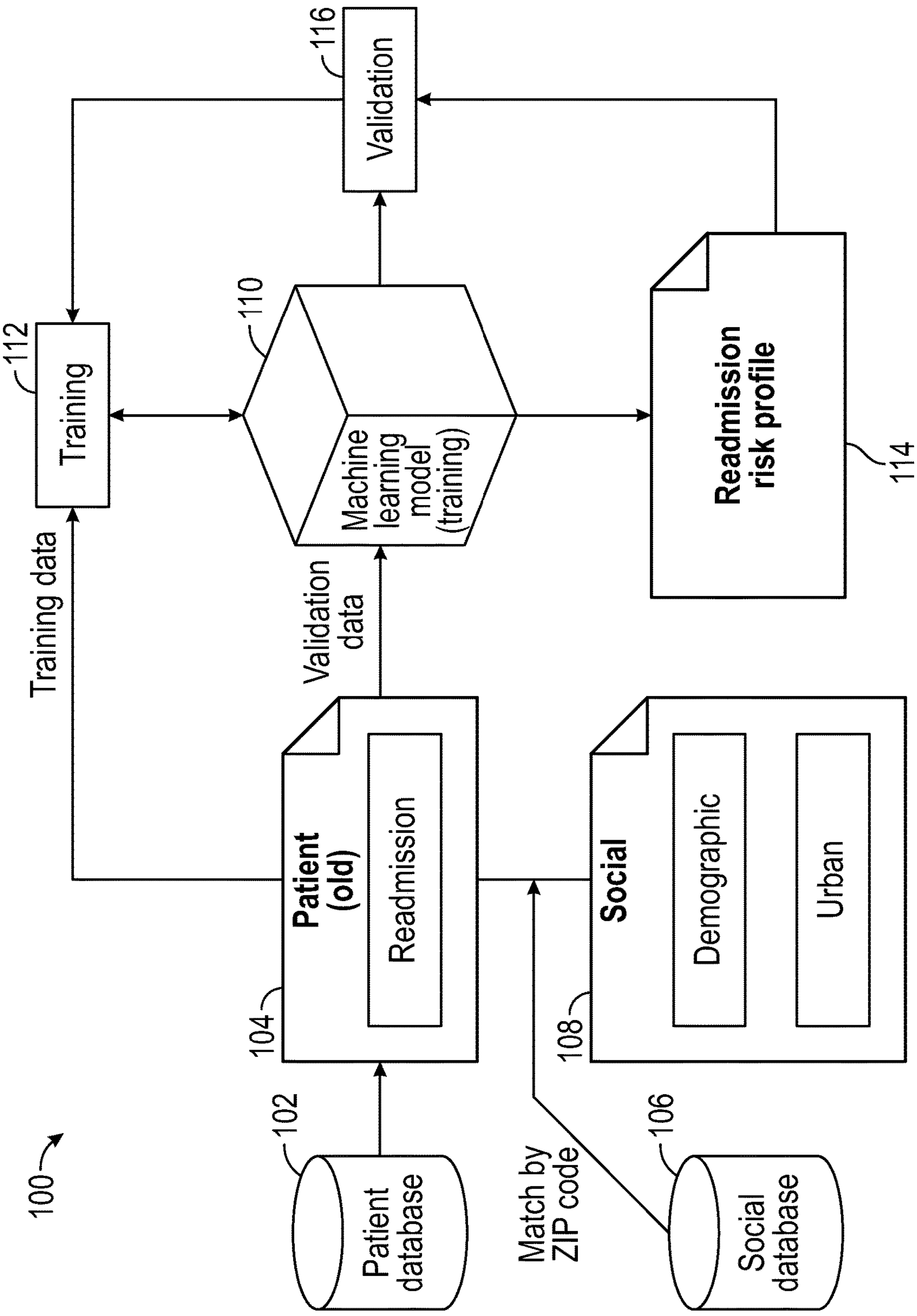
FIGS. 1A-1B are data flow diagrams of a risk modeling system for patient readmissions to a healthcare facility, according to some embodiments presented in this disclosure.

Embodiments presented in this disclosure provide a risk modeling system that applies machine learning to predict whether a patient is at risk of readmission to a healthcare facility after the patient is discharged from the healthcare facility. To that end, the risk modeling system maps patient information to social information from one or more social data sources. The mapping is performed based on residential information included in the patient information. The social information includes at least one of demographic information and urban information.

The risk modeling system then uses the patient information and social information to predict whether the patient is at risk of readmission to the healthcare facility. By taking the social information into account, the risk modeling system can generate predictions that, at least in some cases, have a greater measure of accuracy at least relative to predictions that do not take the social information into account. For instance, potential false negatives can be identified, whereas potential false positives can be disqualified. At least in such instances, embodiments disclosed herein achieve the technical advantage of increased prediction accuracy of machine learning models, thereby improving the technical field of machine learning to predict patient risks.

At least in some embodiments, the predictions are generated in the form of a readmission risk profile for the patient. The risk modeling system then generates for display a graphical user interface that includes an indication of the readmission risk profile. Because the readmission risk profile identifies whether a patient is at risk of readmission, proactive remedial actions can be taken to reduce the risk of readmission. Depending on the type of remedial action, the remedial action can be taken by the personnel of the healthcare facility and/or by the risk modeling system.

The readmission risk profile can be mapped to these remedial actions by the risk modeling system, in some embodiments. These remedial actions can include treatment plans that involve administering additional or modified medical treatments to the patient, based on the predictions of increased accuracy. At least in these instances, embodiments disclosed herein cause a particular treatment or prophylaxis to be effected for preventing or reducing an incidence or extent of illness or injury, of patients following discharge from a healthcare facility, that would result in readmissions to the healthcare facility. Advantageously, embodiments disclosed herein lower the patient readmission rate of the healthcare facility, thereby improving quality of care and patient outcomes of the healthcare facility.

Although embodiments herein are described with reference to supervised machine learning techniques, such descriptions are merely exemplary and do not limit the embodiments disclosed herein. Other embodiments are broadly contemplated, such as unsupervised machine learning techniques or a combination of supervised and unsupervised machine learning techniques.

Figure 1B:
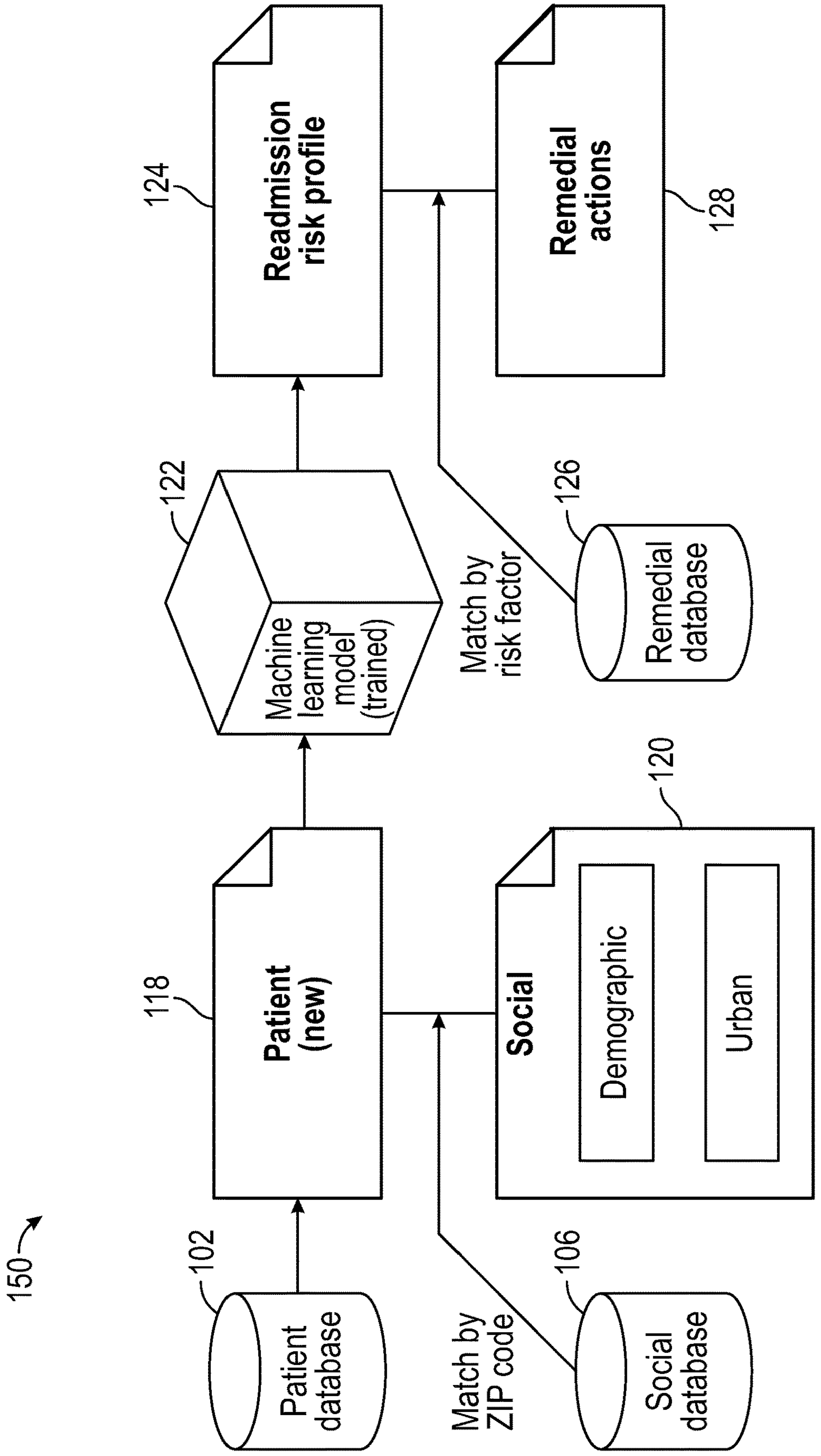

FIGS. 1A-1B are data flow diagrams of a risk modeling system for patient readmissions to a healthcare facility, according to some embodiments. Depending on the embodiment, the healthcare facility can be a skilled nursing center, an assisted living facility, a hospital, a rehabilitation center, a surgery center, or the like.

Example Data Flow for Training a Risk Modeling System

Referring to FIG. 1A, a data flow diagram that illustrates training of a risk modeling system 100 for patient readmissions to a healthcare facility according to one embodiment is shown. In one embodiment, the risk modeling system 100 retrieves patient information 104 in the form of patient records from a patient database 102, in one embodiment. To facilitate training, the patient information 104 can be limited to information pertaining to patients previously discharged from the healthcare facility and for which their readmission status has been determined.

For instance, a patient can be considered as not having been readmitted if the patient is not readmitted to the healthcare facility within a threshold period of time, e.g., two weeks, since being discharged from the healthcare facility. In some embodiments, the threshold period of time can be longer or shorter depending on the reason that the patient originally stayed at the healthcare facility. For instance, if the patient stayed at the facility following a urinary tract information, the threshold can be one week, whereas if the patient stayed at the facility following joint replacement surgery, the threshold can be four weeks.

Although embodiments are described with reference to using a single machine learning model to model risk of patient readmissions to a single healthcare facility, such descriptions are merely exemplary and do not limit embodiments disclosed herein. Those skilled in the art will recognize that other embodiments are broadly contemplated, such as using multiple machine learning models and/or modeling risk of patient readmissions for multiple healthcare facilities. Depending on the embodiment, these healthcare facilities can belong to the same healthcare provider or different healthcare providers.

In the case of modeling risk for multiple healthcare facilities, a separate machine learning model can be trained and deployed for each healthcare facility and/or healthcare provider, in one embodiment. Additionally or alternatively, in some embodiments, a separate machine learning model can be trained and deployed for each distinct categorization, or combination of categorizations, that is desired to be modeled. Each categorization can be based on an information type that is included in the patient information. In this regard, each information type can correspond to a respective field in a patient record.

As an example, a separate machine learning model can be trained and deployed for each distinct combination of healthcare facility, geographical region, and patient gender. The reason for having multiple machine learning models in this manner can be to better account for differences in characteristics between different healthcare facilities, different geographical regions, and/or different patient genders. As such, doing so can yield machine learning models better tailored to make accurate predictions for specific categorizations, at least in some cases. Those skilled in the art will recognize that the number and types of machine learning models trained and deployed can be tailored to suit the needs of a particular case.

Although embodiments are described with reference to a single risk modeling system that trains and uses the machine learning model, such descriptions are merely exemplary and do not limit embodiments disclosed herein. Other embodiments are broadly contemplated, such as a first risk modeling system that trains the machine learning model before deploying, over a network, the trained machine learning model for use by a second risk modeling system.

In one embodiment, the risk modeling system 100 matches the patient information 104 to corresponding social information 108 from a social database 106. The social database 106 contains, for each of a number of different geographical region, social information specific to the respective geographical region. The social information includes demographic information and/or urban information. Depending on the embodiment, the social information, demographic information, and urban information can be represented in the form of social records, demographic records, and urban records, respectively.

In some embodiments, the match is based on residential information included in the patient information 104. For instance, the match can be performed by executing a relational database query that includes an inner join to correlate patient information with social information based on the residential information. At least in some embodiments, the match is performed without involving the machine learning model 110. Examples of residential information include residential address, ZIP code, city of residence, county of residence, state of residence, country of residence, census tract, phone area code, and the like. In the example shown, the match is performed by ZIP code. The social information 108 pertains to a geographical region corresponding to the residential information included in the patient information 104.

The matching can be performed in various ways, depending on the embodiment. In one embodiment, a ZIP code in the residential information is matched with a ZIP code in the social information 108. In some cases, however, the social database 106 may not include any social information pertaining to the ZIP code. Additionally or alternatively, the ZIP code in the residential information of the patient can be invalid, missing, or otherwise unspecified.

In these instances, the risk modeling system 100 can evaluate other fields in the residential information and/or in the social database in order to identify a match. In doing so, the risk modeling system 100 can iteratively and gradually enlarge the geographical region for the residential information and/or for the social information, until a match is found or, if the geographical regions cannot be enlarged any further or has otherwise reached a threshold geographical scope, conclude that no match exists. To determine which regions encompass which other regions, the risk modeling system 100 can query one or more lookup tables, in one embodiment. These lookup tables can be stored in a geographical database.

For example, the risk modeling system 100 can further query the social database 106 for social information pertaining to a next largest encompassing geographical region, such as a city encompassing the ZIP code. If a match is found, the risk modeling system then correlates the social information with the residential information that includes the ZIP code. If no match is found, however, the social database 106 can be still further queried for social information pertaining to a county encompassing the city. If a match is still not found, the social database 106 can be even still further queried for social information pertaining to a state encompassing the county. If no match is found, another query can be submitted for a region encompassing the state (e.g., the Midwest), in one embodiment.

If the threshold geographical scope is set to country (e.g., U.S.), and no match is found for the region, the risk modeling system 100 can conclude that no match is found whatsoever, even if the social database 106 contains social information pertaining to the country as a whole (e.g., U.S.), in one embodiment. Alternatively, if the threshold is set to an even larger region, such as a continent (e.g., North America) or the world, the social information pertaining to the country can be deemed as a match for the ZIP code.

Similarly, if the ZIP code in the residential information of the patient is invalid, missing, or unspecified, the risk modeling system 100 can query the social database 106 for social information pertaining to a city that matches a city specified in the residential information, in one embodiment. Suppose that no match is found based on the city. If the residential information does not specify any county information (e.g., because county information is not collected from patients), the risk modeling system 100 can query the lookup tables to identify a county corresponding to the city, in one embodiment. The social database 106 can then be queried for social information pertaining to the county, even though the county is not specified in the residential information of the patient.

In some embodiments, the social database 106 contains data obtained from one or more social data sources pertaining to social determinants of health. At least in some embodiments, social determinants of health refer to any non-medical factors that affect health outcomes. In this regard, the social determinants of health can broadly include the conditions in which people grow, live, and age, as well as factors that shape those conditions, such as economic, social, and political systems and policies.

Examples of social data sources include U.S. Census Data and Statistics, Chronic Disease Indicators, Chronic Kidney Disease (CKD) Surveillance System, and Compendium of Federal Datasets Addressing Health Disparities. Additional examples include Disability and Health Data System (DHDS); PLACES: Local Data for Better Health; and Interactive Atlas of Heart Disease and Stroke. Still other examples include National Center for HIV, Viral Hepatitis, STD, and TB Prevention (NCHHSTP) AtlasPlus; National Environmental Public Health Tracking Network; Social Vulnerability Index; and Vulnerable Populations Footprint Tool.

In one embodiment, the risk modeling system 100 divides the patient records into discrete sets of data including a first set containing training data and a second set containing validation data. In this regard, the patient records can be divided into the discrete sets of data in any suitable manner. For example, the risk modeling system 100 can divide the patient records randomly into the training data and the validation data. As another example, the risk modeling system 100 can select, from the patient records, data points that differ the most from one another, to form the training data. In some embodiments, the risk modeling system 100 clusters the data points in the patient records so that data points most similar to one another are assigned to the same cluster. The risk modeling system 100 then selects data points from different clusters to form the training data. As a result, the training data features a more diverse set of data points, which can improve the robustness and accuracy of a machine learning model trained using the training data, at least in some cases. After forming the training data, the remaining data points in the patient records can be used to form the validation data.

The risk modeling system 100 then trains a machine learning model 110 using the training data, in block 112, in one embodiment. In particular, the machine learning model is trained to predict a readmission risk of a patient based on the patient information 104 and the corresponding social information 108. During training, the risk modeling system 100 uses the machine learning model 110 to analyze the data points in the training data. The machine learning model detects patterns or trends in the data points of the training data and learns particular readmission risk profiles, including risk levels and/or risk factors, that correspond to or result from these detected patterns or trends. In this manner, the machine learning model 110 is trained to predict the likelihood of patient readmissions when certain patterns or trends are detected.

Once the machine learning model 110 is trained, the risk modeling system 100 validates the machine learning model 110 based on the validation data, in block 116, in one embodiment. To that end, the machine learning model 110 generates, based on the validation data, predictions in the form of a readmission risk profile 114 of each patient reflected in the validation data. These predictions are generated based on the patterns or trends detected by the machine learning model 110. The readmission risk profile 114 is then compared to readmission information, of the patient information, that is included in the validation data. If the validation indicates that the machine learning model 110 has been trained to a measure of accuracy that satisfies a threshold accuracy level, training concludes; otherwise, additional training commences in block 112. It should be noted that the embodiments described herein are not limited to any particular type of machine learning model. Depending on the embodiment, the machine learning model can be any of various types of neural networks.

Example Data Flow for Applying the Risk Modeling System

Referring to FIG. 1B, a data flow diagram that illustrates application of a risk modeling system 150 for patient readmissions to the healthcare facility according to one embodiment is shown. In one embodiment, the risk modeling system 150 retrieves patient information 118 in the form of a patient record from the patient database 102. The patient information 118 can include information pertaining to a patient admitted for a new stay at the healthcare facility and who has not yet been discharged. The risk modeling system 150 matches the patient information 118 to corresponding social information 120 from the social database 106, where the social information 120 includes demographic information and/or urban information. The match can be performed based on residential information, such as ZIP code, included in the patient information 118. At least in some embodiments, the match is performed without involving the machine learning model 122.

In one embodiment, the risk modeling system 150 applies the trained machine learning model 122 to determine a readmission risk profile 124 of a patient reflected in the patient information 118. The risk modeling system 150 then matches the readmission risk profile with remedial information retrieved from a remedial database 126 and outputs the readmission risk profile for display. For instance, the match can be performed by executing a relational database query that includes an inner join to correlate the readmission risk profile 124 with remedial information based on information, such as risk factors and/or risk levels, specified in the readmission risk profile 124. In some embodiments, the remedial information can be matched by the risk modeling system 150 without involving the machine learning model 122. In other embodiments, the remedial information is determined using the machine learning model 122 or a different machine learning model, such as one that is specifically trained to predict remedial information. In still other embodiments, the risk modeling system 150 altogether refrains from determining remedial information that matches the readmission risk profile.

In some embodiments, the remedial information specifies remedial actions 128 that should be taken by the healthcare facility in view of the readmission risk profile 124. Examples of remedial actions include providing modified or additional treatment or services to the patient, notifying the patient of recommended actions to be taken by the patient following discharge, and/or coordinating with additional parties, such as a social worker, friend, family member, and/or acquaintance, to monitor, assess, and/or support the well-being of the patient following discharge. In one embodiment, the risk modeling system 150 updates the patient information 118 to reflect the readmission risk profile 124 and/or the corresponding remedial information.

Depending on the type of remedial action, the remedial actions can be performed before and/or after the patient is discharged from the healthcare facility. Further, depending on the type of remedial action, the remedial actions can be performed by personnel of the healthcare facility and/or a computing system of the healthcare facility (e.g., the risk modeling system 150). For instance, a remedial action of merely notifying a patient of a recommendation can be performed by the personnel (e.g., by speaking with the patient) and/or by the risk modeling system 150 (e.g., by causing an automated text message to be sent to a mobile device of the patient).

Although the patient database 102, the social database 106, and the remedial database 126, the geographical database, and the medical database are depicted and/or described as discrete databases, in some embodiments, data from the patient database 102, the social database 106, the remedial database 126, the geographical database, and the medical database can be stored in a single database or across multiple databases of a number greater than or less than five.

In some embodiments, specified types of information in the patient information can be withheld as an input to training and/or use of the machine learning model because the types of information are deemed as bearing limited or reduced relevance to prediction accuracy. For example, patient name and/or patient social security number can be withheld from the machine learning model or otherwise redacted or removed from the patient database altogether. Doing so can protect patient information privacy while improving processing efficiency of training or using the machine learning model, at least in some cases.

As another example, patient information pertaining to healthcare facility stays that are chronologically older than a threshold cutoff date can be withheld from training data for the machine learning model. As a result, the machine learning model is trained using newer data as opposed to outdated data, which can improve the prediction accuracy of the machine learning model at least in some cases.

Example Workflow to Preprocess Unstructured Data to Improve Machine Learning In some embodiments, to improve the processing efficiency of the machine learning model during its training or use, the risk modeling system can perform one or more parsing operations to preprocess the patient information, social information, and/or remedial information. Doing so can make the information more compatible with natural language processing and, hence, more suitable for consumption by the machine learning model.

Figure 2:
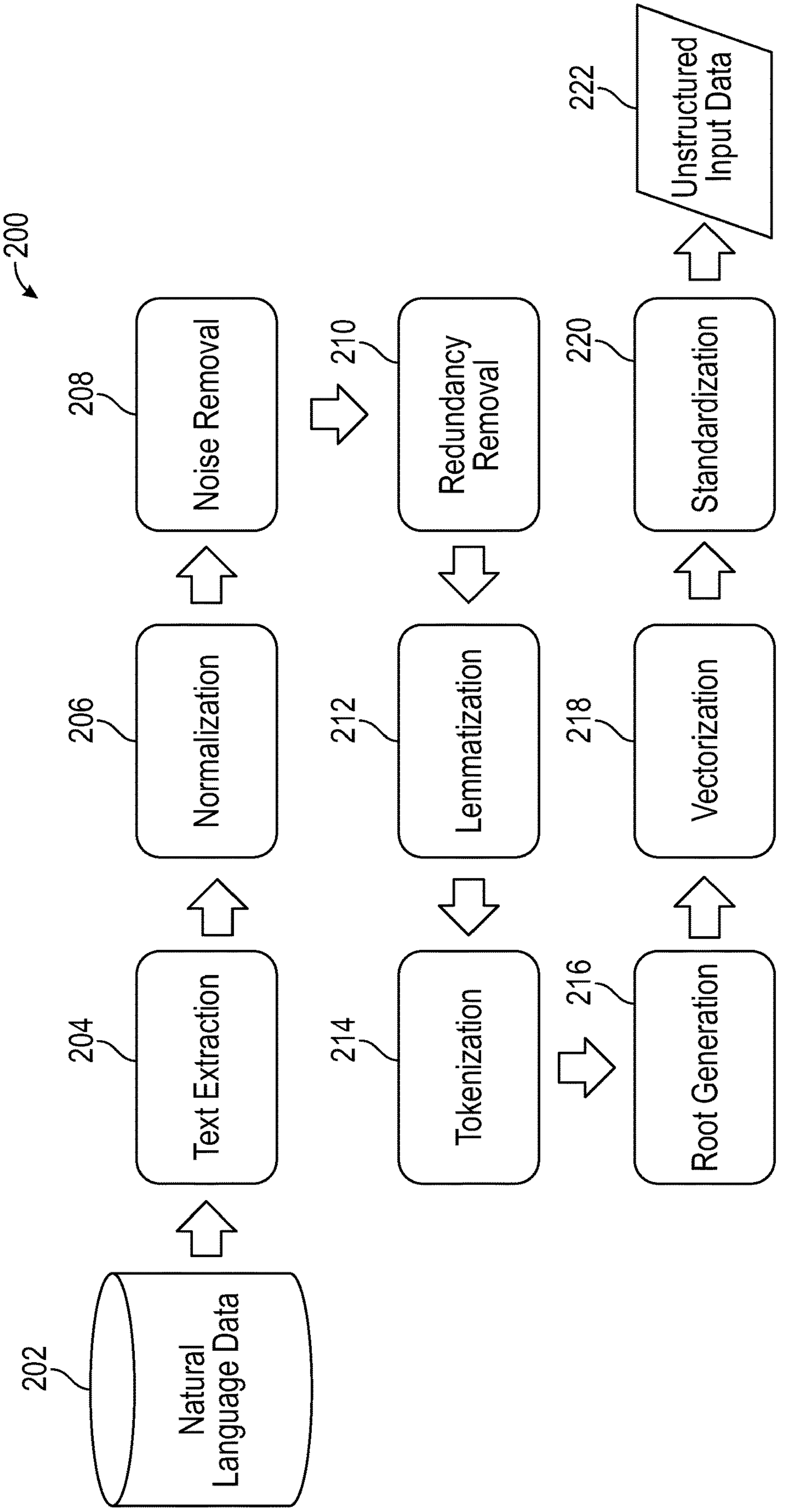
FIG. 2 depicts a workflow for preprocessing unstructured data for improved machine learning, according to one embodiment.

FIG. 2 depicts a workflow 200 for preprocessing unstructured data for improved machine learning, according to one embodiment. In some embodiments, the workflow 200 can be performed to process natural language data 202 for input to one or more machine learning models. Depending on the embodiment, the workflow 200 can be performed by the risk modeling system 100 of FIG. 1A, the risk modeling system 150 of FIG. 1B, or other systems such as dedicated natural language processing or preprocessing systems and/or one or more remote systems, e.g., a cloud-based service.

The workflow 200 can be used for training machine learning models, e.g., to generate training data, and/or for inferencing using the models, e.g., as input to generate a predicted readmission risk profile. That is, the workflow 200 can be used to transform or preprocess any natural language input before providing the natural language input as an input to the machine learning model.

As shown in the workflow 200, natural language data 202 is received for processing to generate unstructured input data 222. In some embodiments, the workflow 200 is referred to as preprocessing to indicate that the workflow 200 is used to transform, refine, manage, or otherwise modify the natural language data 202 to improve its suitability for use with machine learning or other downstream processing. In some embodiments, the natural language data 202 corresponds to notes that are authored by a member of a healthcare facility (e.g., a physician) and that pertain to patient readmission (e.g., information relating to reasons for readmission).

As such, the workflow 200 can be used to preprocess natural language data extracted from written notes, such as notes regarding the readmission of a patient and authored by a physician, according to one embodiment. This extracted text can be ultimately processed to glean insights useful for predicting readmission risk profiles for patients. At least in some embodiments, however, it can be advantageous to first perform preprocessing operations on the extracted text according to the techniques presented in this disclosure.

Advantageously, preprocessing the data in the natural language notes 202 can improve the training process of machine learning models at least in some cases, by making the data more compatible with natural language processing and, hence, better suited for consumption by the machine learning model during training. Preprocessing can generally include a variety of operations. Although the illustrated workflow 200 depicts a series of operations being performed sequentially for conceptual understanding, in embodiments, some or all of the operations can be performed in parallel. Similarly, in some embodiments, the workflow 200 can include additional operations not depicted and/or can include a subset of the depicted operations.

At least in some embodiments, the natural language data 202 first undergoes undergo text extraction 204 in the workflow 200. The text extraction 204 can generally correspond to extracting natural language text from an unstructured portion of the natural language data 202, according to one embodiment. For example, if the natural language data 202 includes a set of notes pertaining to a patient, the text extraction 204 can include identifying and extracting these notes for evaluation. In some aspects, the notes can further include structured or semi-structured data that can undergo more traditional processing as needed. Such structured or semi-structured data can include a timestamp indicating when the note was written or revised, an indication of the specific patient about whom the note was written, an indication of the author of the note, and the like.

In one embodiment, normalization 206 in the workflow 200 can generally include a wide variety of text normalization processes, such as converting all characters in the extracted text to lowercase, converting accented characters to unaccented characters, expanding contractions, converting words to numeric form where applicable, converting dates to a standard date format, and so forth.

Noise removal 208 in the workflow 200 can generally include identification and removal of portions of the extracted text that do not carry meaningful or probative value, according to one embodiment. That is, noise removal 208 can include removing characters, portions, or elements of the text that are not useful or meaningful in the desired computing task, such as predicting a readmission risk profile, and/or that are not useful to human readers. For example, the noise removal 208 can include removing extra white or blank spaces, tabs, or lines, removing markup language tags, and so on.

In one embodiment, redundancy removal 210 in the workflow 200 can generally correspond to identifying and eliminating or removing text corresponding to redundant elements (e.g., duplicate words) and/or the reduction of a sentence or phrase to a portion thereof that is more suitable for training or applying a machine learning model. For example, the redundancy removal 210 can include eliminating verbs, conjunctions, or other extraneous words, that do not aid the machine learning task.

Lemmatization 212 in the workflow 200 can generally include stemming and/or lemmatization of one or more words in the extracted text, according to one embodiment. This can include converting words from their inflectional or other form to a base form. For example, lemmatization 212 can include replacing "holding," "holds," and "held" with the base form "hold."

In one embodiment, tokenization 214 in the workflow 200 includes transforming or splitting elements in the extracted text into smaller elements, also referred to as "tokens." For example, the tokenization 214 can include tokenizing a paragraph into a set of sentences, tokenizing a sentence into a set of words, transforming a word into a set of characters, splitting strings of text into smaller strings, and the like. In some embodiments, the tokenization 214 can additionally or alternatively refer to the replacement of sensitive data with placeholder values for downstream processing. For example, text such as the personal address of the user can be replaced or masked with a placeholder (referred to as a "token" in some aspects), allowing the remaining text to be evaluated without exposing this private information.

Root generation 216 in the workflow 200 can include reducing portion of the extracted text (e.g., a phrase or sentence) to its most relevant n-gram (e.g., a bigram) or root for downstream operations involving training or applying the machine learning model, according to one embodiment.

In one embodiment, vectorization 218 in the workflow 200 can generally include converting the text into one or more objects that can be represented numerically, e.g., into a vector or tensor form. For example, the vectorization 218 can use one-hot encodings, e.g., where each element in the vector indicates the presence or absence of a given word, phrase, sentiment, or other concept, based on the value of the element. In some embodiments, the vectorization 218 can correspond to any word embedding vectors. These word embedding vectors can be generated using all or a portion of a trained machine learning model, e.g., initial layers of a feature extraction model. This resulting object can then be processed by downstream natural language processing algorithms or machine learning models to improve the ability of the risk modeling system to evaluate the text. Doing so can drive prediction accuracy, of the risk modeling system, as to readmission risk profiles of patients at least in some cases.

Standardization 220 in the workflow 200 can generally include any parsing operation that processes the patient information, social information, and/or remedial information to improve a measure of consistency of data across records themselves and/or against standardized information contained in one or more databases, according to one embodiment. In one example, the standardization operation can use natural language processing to identify derivatives of medical diagnoses and/or treatments reflected in the patient information and/or associated social information. In some embodiments, the medical diagnoses and/or treatments can be reflected in medical information, stay information, and/or readmission information, which are further described below in conjunction with FIGS. 3 and 5-7.

For instance, one patient record can list a diagnosis of "high blood pressure," while another patient record can list a diagnosis of "hypertension." Using natural language processing and the medical database, the risk modeling system can determine that the diagnosis of high blood pressure matches the diagnosis of hypertension. As a result, the risk modeling system can modify the patient records so that both patient records refer to the diagnosis using the same term (e.g., high blood pressure).

Other examples of inconsistencies in the data include singular versus plural references to diagnoses or treatments, alternate wording or phrasing of diagnoses or treatments, and so on. In some embodiments, the natural language processing can be performed via its own machine learning model that is separate from those configured to predict readmission risk profiles of patients. Depending on the embodiment, the training and/or use of that such machine learning model can be based on information contained in a medical database. In this manner, data contained in records of the patient information, social information, and/or remedial information do not necessarily need to match precisely in order to be recognized by the machine learning model during its training or use, provided that the standardization operation is first performed.

Accordingly, the various preprocessing operations in the workflow 200 result in the unstructured input data 222 being generated at least in some embodiments. That is, the unstructured input data 222 corresponds to the unstructured natural language data 202 after it has undergone various preprocessing operations to improve its use with downstream machine learning models. The workflow 200 can generally include any other suitable techniques for making text ingestion more efficient or accurate, either for a training phase of a machine learning model or for generating an inference or prediction using a trained model. Advantageously, improving results of the natural language processing algorithm can increase the processing efficiency and/or prediction accuracy of the machine learning model at least in some cases.

Figure 3:
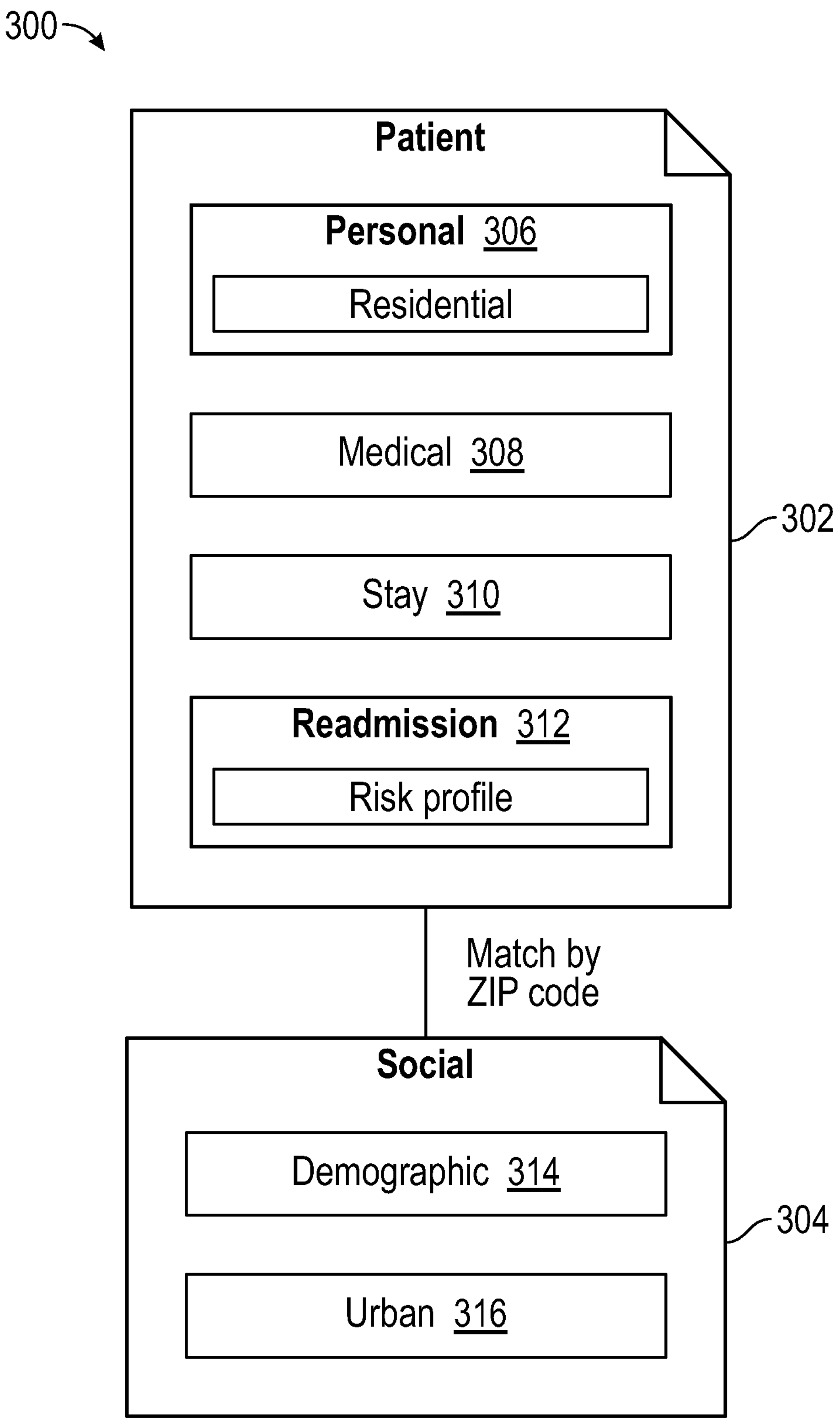
FIG. 3 is a block diagram of patient information that is correlated with social information based on residential information, according to one embodiment.

Example Types of Patient Information and Social Information for Risk Modeling FIG. 3 is a block diagram 300 of patient information 302 that is correlated with social information 304 based on residential information, according to one embodiment. As shown, the patient information 302 includes personal information 306, medical information 308, stay information 310, and readmission information 312. The readmission information 312 includes a readmission risk profile determined by the machine learning model. As shown, the patient information 302 is matched with the social information 304 based on ZIP code, and the social information 304 includes demographic information 314 and urban information 316.

At least in some embodiments, patient records containing the patient information 302 can be augmented to include the social information 304 such that the augmented records are stored in the patient database. Doing so can improve processing efficiency by avoiding a processing cost associated with re-correlating the patient information 302 with the social information 304 responsive to subsequent requests for the correlated information. In other embodiments, no augmented patient records are stored in the patient database, and the patient information is re-correlated with the social information 304 on demand.

The types of information included in the patient information 302 and the social information 304 are further described in conjunction with FIGS. 4-9, according to some embodiments. It should be noted that the number and types of information directly or indirectly included in the patient information 302 and the social information 304 are described in FIGS. 3-9 for illustrative purposes only and do not limit embodiments disclosed herein. Those skilled in the art will recognize that the number and/or types of information can be tailored to suit the needs of a particular case.

Figure 4:
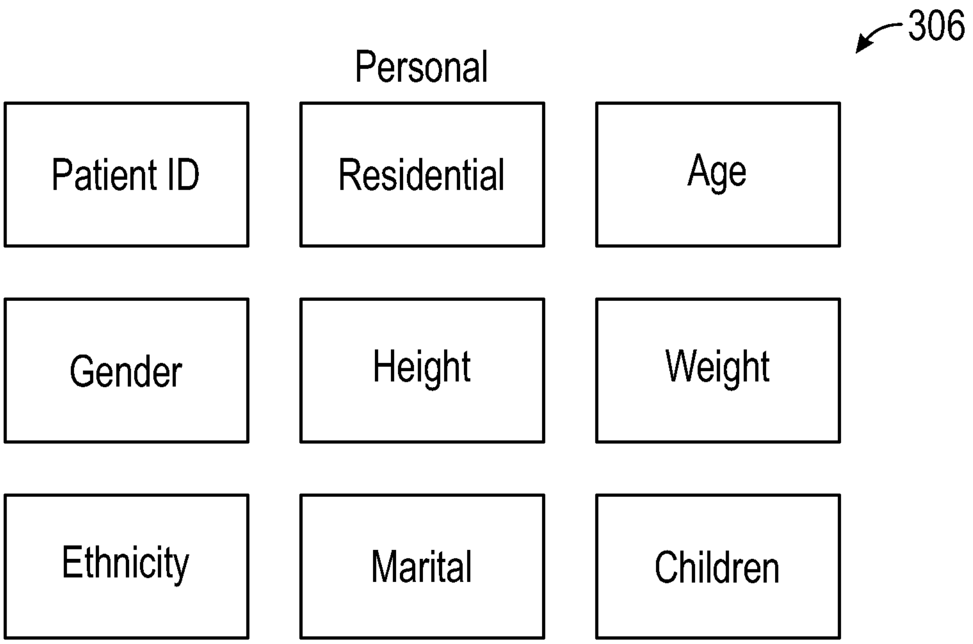
FIG. 4 is a block diagram of personal information that is included in the patient information, according to one embodiment.

FIG. 4 is a block diagram of the personal information 306 that is included in the patient information, according to one embodiment. As shown, the personal information 306 includes a patient identifier of the patient, residential information of the patient, age information of the patient (e.g., date of birth), and a gender of the patient. The personal information 306 also includes a height of the patient and a weight of the patient. The personal information 306 further includes an ethnicity of the patient, a marital status of the patient, and a number of children of the patient. Depending on the embodiment, other types of personal information can be included. Such other types can include work industry, occupation, nationality, religion, political affiliation, organizational affiliation, sexual orientation, contact information (e.g., phone number or email address), and the like.

Figure 5:
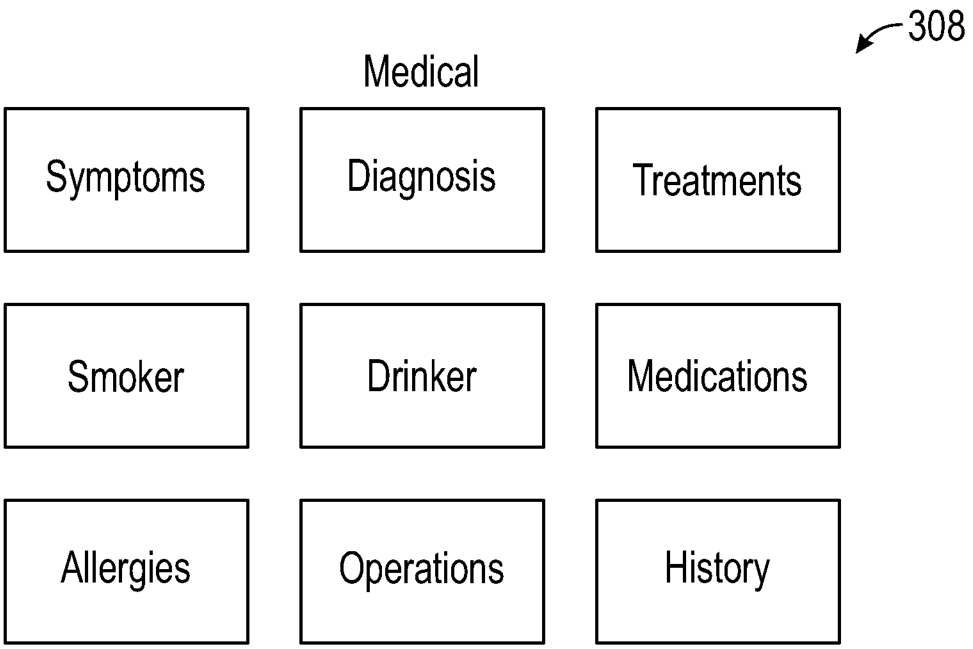
FIG. 5 is a block diagram of medical information that is included in the patient information, according to one embodiment.

FIG. 5 is a block diagram of the medical information 308 that is included in the patient information, according to one embodiment. As shown, the medical information 308 includes symptoms of the patient, a diagnosis of the patient, treatments prescribed and/or given to the patient, whether the patient is a smoker of tobacco products, whether the patient is a drinker of alcoholic beverages, medications that the patient is taking, known allergies of the patient, operations previously performed on the patient, and a medical history of the patient and/or his family. The medical information 308 can be represented in the form of a Continuity of Care Document (CCD), an Electronic Health Record (EHR), patient notes, and the like.

Depending on the embodiment, other types of medical information can be included. Such other types can include vaccination information, whether the patient wears a seatbelt, whether the patient wears a motorcycle helmet, whether the patient is sexually active, types of contraceptives used by the patient, types of sterilization procedures performed, whether the patient uses recreational drugs, and for female patients, whether the patient is pregnant and whether the patient has previously undergone a C-section.

Figure 6:
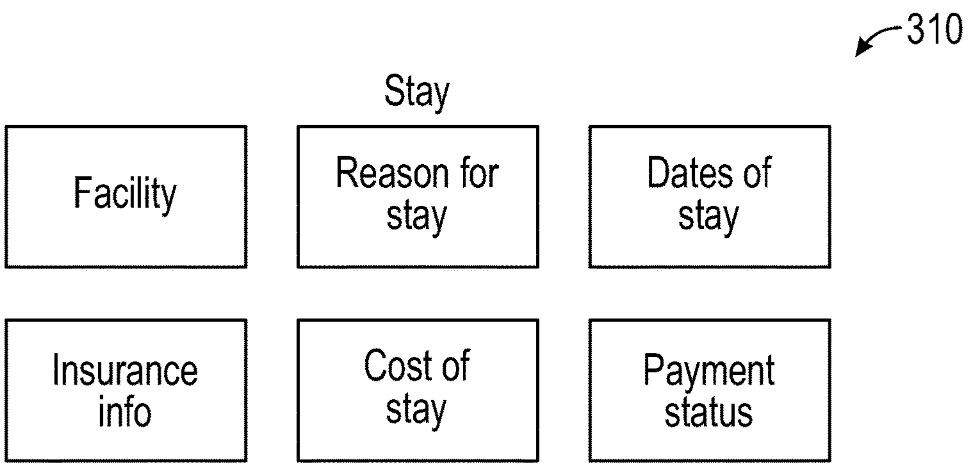
FIG. 6 is a block diagram of stay information that is included in the patient information, according to one embodiment.

FIG. 6 is a block diagram of stay information 310 that is included in the patient information, according to one embodiment. As shown, the stay information 310 includes identification of the healthcare facility, a reason that the patient is (or was) staying at the healthcare facility (e.g., the diagnosis and/or the associated treatment for the patient), dates of stay of the patient at the healthcare facility, medical insurance information of the patient, a cost of the stay of the patient at the healthcare facility, and a payment status of the patient for the stay at the healthcare facility. The medical insurance information of the patient can include information pertaining to government healthcare participant information and/or private insurance participant information.

Figure 7:
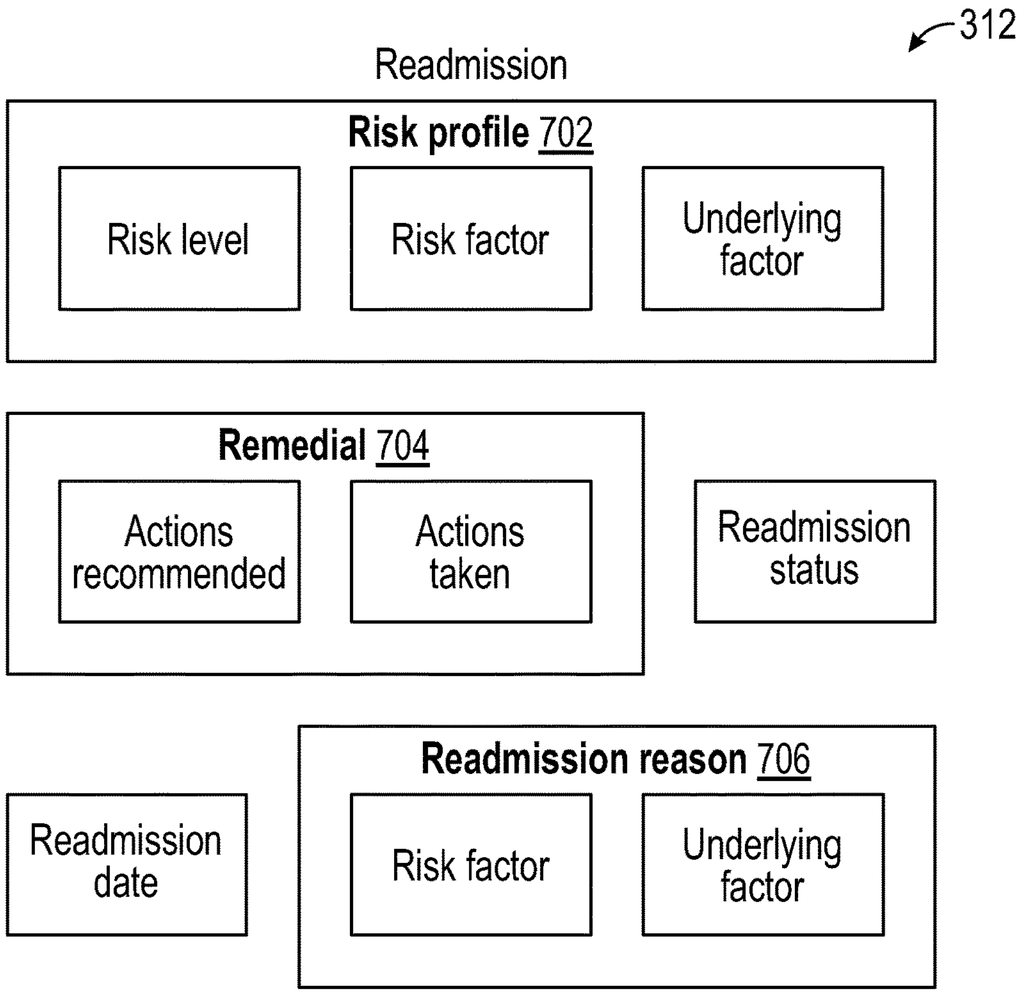
FIG. 7 is a block diagram of readmission information that is included in the patient information, according to one embodiment.

FIG. 7 is a block diagram of readmission information 312 that is included in the patient information, according to one embodiment. As shown, the readmission information 312 includes a readmission risk profile 702 of the patient, remedial information 704 corresponding to the risk profile 702, a readmission status of the patient following discharge, and, if the patient is readmitted, a readmission date of the patient and a readmission reason 706 of the patient. The risk profile 702 includes a readmission risk level of the patient, a readmission risk factor associated with the readmission risk level, and an underlying factor associated with the readmission risk factor. In instances where multiple readmission risk factors, each with a respective risk level, are identified, an overall readmission risk level of the patient can be determined and included in the readmission risk profile 702. In some embodiments, additional layers of underlying factors can be included.

The remedial information 704 includes indications of remedial actions, associated with the readmission risk profile 702, that are recommended to be taken by the healthcare facility and further includes indications of which of the recommended remedial actions have been taken by the healthcare facility. The readmission reason 706 specifies a risk factor and/or an underlying factor responsible for readmission of the patient to the healthcare facility following discharge. Depending on the embodiment, the risk factor and/or underlying factor in the readmission reason 706 can be among those identified in the risk profile 702 or can be ones that were not identified in the risk profile 702.

Figure 8:
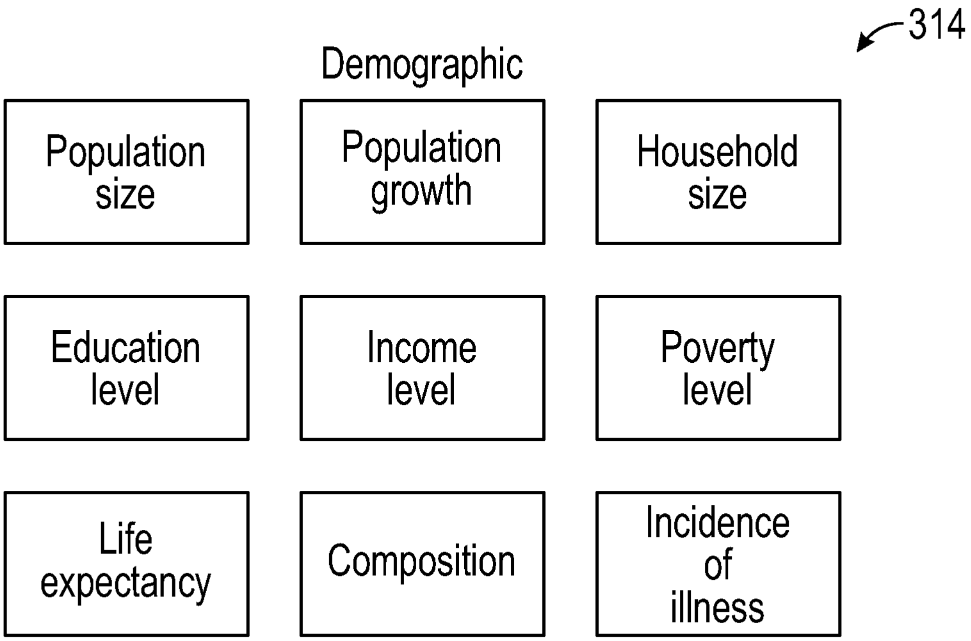
FIG. 8 is a block diagram of demographic information that is included in the social information, according to one embodiment.

FIG. 8 is a block diagram of demographic information 314 that is included in the social information, according to one embodiment. As shown, the demographic information 314 includes a population size of a geographical region associated with the residential information of the patient, a population growth of the geographical region, a household size of the geographical region, an education level of the geographical region, an income level of the geographical region, a poverty level of the geographical region, a life expectancy of the geographical region, a demographic composition of the geographical region, and an incidence of illness of a specified type in the geographical region. In some embodiments, the demographic composition of the geographical region can include ethnic composition, age composition, gender composition, work industry composition, occupation composition, religious composition, political composition, and the like.

At least in some embodiments, the patient information is only correlated with types of social information that are non-existent in the patient information. The reason for this is because correlating the patient information with types of social information that already exist in the patient information would only add less-precise information to more-precise information. In such scenarios, the added information may not necessarily improve the accuracy, of the machine learning model in predicting readmission risk profiles patients, nearly as much as in scenarios where the types of social information being added are non-existent in the patient information.

For example, in some embodiments, certain types of demographic information, such as an age composition of the geographical region and a gender composition of the geographical region, are withheld from the machine learning model, because such information would be less accurate than personal information of the patient, namely, patent age and patient gender. In other embodiments, however, these types of demographic information can nevertheless be used by the machine learning model in certain instances. Such instances can include those where such types of information are absent, invalid, or otherwise unspecified in the personal information of the patient, such as missing information, erroneous information, or types of information that are not collected. Such instances can also include those where it is desired to model health correlations based on aggregate versions of information types already included in patient information.

For example, a young patient could nevertheless have a different readmission risk if residing in a geographical region having an older age composition as opposed to a younger age composition, such as due to a confounding variable. As another example, a young patient could nevertheless have a different readmission risk if residing in a geographical region having an older age composition as opposed to a younger age composition. Similarly, a patient who is not obese could nevertheless have a different readmission risk if residing in a geographical region having a higher incidence of obesity as opposed to a lower incidence of obesity.

Figure 9:
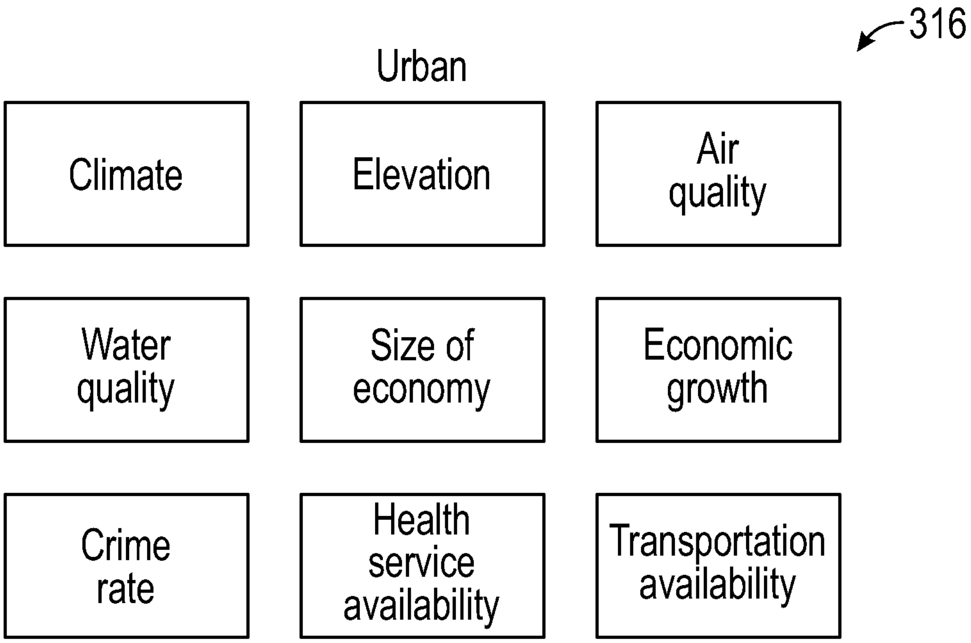
FIG. 9 is a block diagram of urban information that is included in the social information, according to one embodiment.

FIG. 9 is a block diagram of urban information 316 that is included in the social information, according to one embodiment. As shown, the urban information 316 includes a climate of the geographical region associated with the residential information of the patient, an elevation of the geographical region, an air quality f the geographical region, a water quality of the geographical region, a size of the economy in the geographical region, a measure of economic growth of the geographical region, a crime rate in the geographical region, a measure of availability of health services in the geographical region, and a measure of availability of transportation services in the geographical region. Depending on the embodiment, other types of urban information can be included, such as availability of social support services (e.g., government support services, charitable support services, community support services, religious support services, and the like).

Readmission Risk Profile Example A

FIGS. 10-13 illustrate readmission risk profiles generated by the risk modeling system, according to some embodiments. Referring to FIG. 10A, the readmission risk profile 1000 generated for a patient in an absence of social information is shown. In this regard, the readmission risk profile 1000 is generated based only on the personal information of the patient. The readmission risk profile 1000 is associated with personal information 1002 and medical information 1004 and includes readmission information. The personal information 1002 includes age information indicating that the patient is elderly. The medical information 1004 includes a diagnosis of the patient as having pneumonia. The readmission information includes a readmission risk level 1006 that characterizes the patient as having a five-percent risk of being readmitted to the healthcare facility after discharge. It should be noted that in the example shown, no determinations as to risk factor and underlying factor are made for the patient by the risk modeling system.

In this example, the five-percent risk is of a specified range between zero percent and one hundred percent. In other embodiments, the readmission risk level can be represented in the form of a number within a specified range of numbers (e.g., a range of numbers between one and ten, with ten representing the greatest risk). The range of numbers can include floating point numbers or can be restricted to integers, depending on the embodiment. The readmission level can be additionally or alternatively represented in the form of a category from a set of predefined categories (e.g., low risk, medium risk, and high risk). Other ways of representing the readmission level are broadly contemplated, such as representing the readmission level in the form of different shapes, symbols, colors, and/or text formatting options.

Figure 10A:
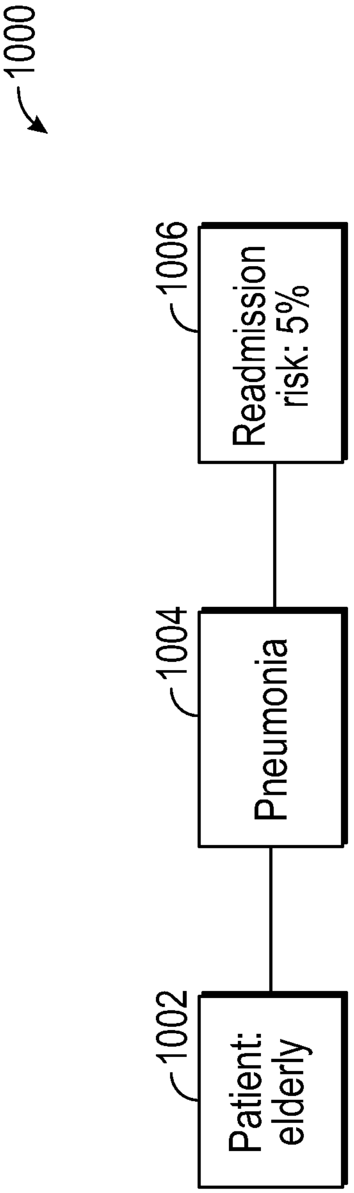
FIGS. 10A-10B illustrate readmission risk profiles generated by the risk modeling system, according to some embodiments.
Figure 10B:
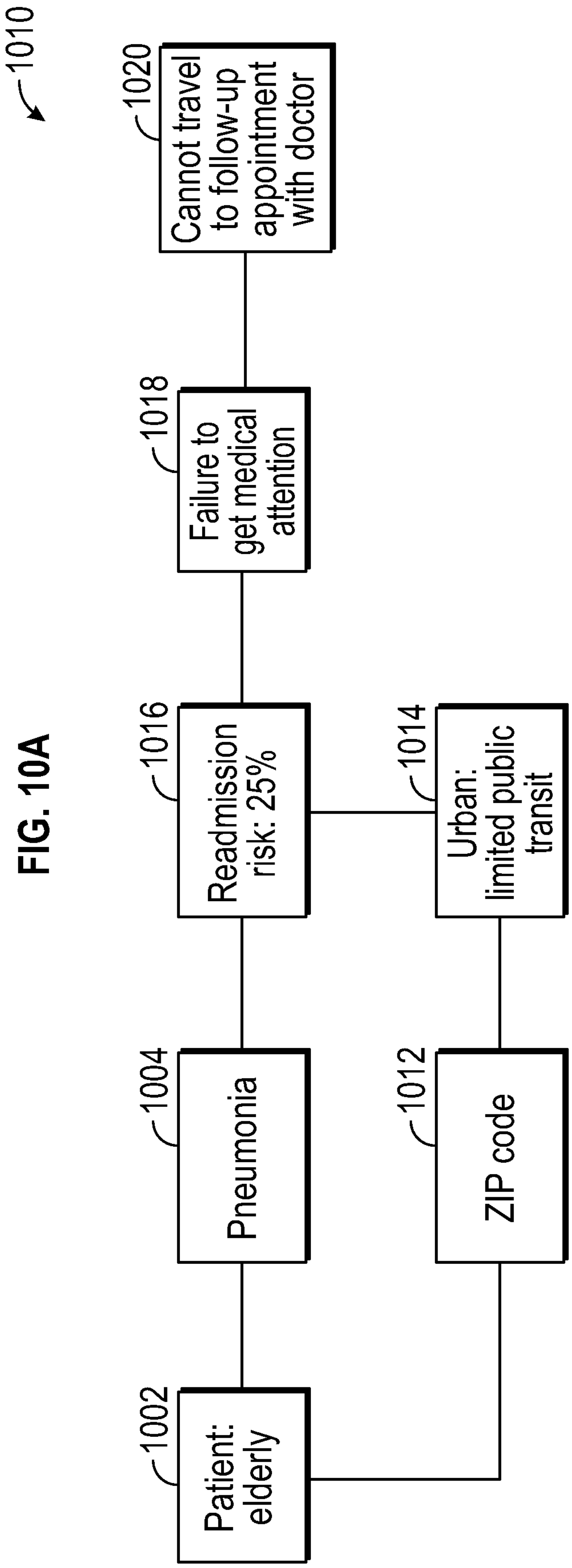

Referring to FIG. 10B, the readmission risk profile 1010 generated for the patient based on social information is shown. The readmission risk profile 1010 is associated with the personal information 1002 and the medical information 1004 and includes readmission risk information. Based on residential information 1012 included in the personal information 1002, the risk modeling system maps patient information of the patient to corresponding social information. As shown, the residential information 1012 includes a ZIP code of the patient. In this example, the social information includes urban information 1014 indicating that the patient resides in a geographical region having limited availability of public transportation.

Based on this additional piece of information that is the urban information 1014, the machine learning model can determine that a readmission risk level 1016 of this patient is heightened as a result of the patient being an elderly individual with limited access to public transportation. This determination can be made based at least in part on the machine learning model having observed other elderly patients, with limited access to public transportation, having higher rates of readmission. The machine learning model can make this determination due to having been trained to both detect patterns or trends in data about previous patients of the healthcare facility and learn whether these patterns or trends resulted in those previous patients being readmitted to the healthcare facility.

Accordingly, the machine learning model can determine a risk factor 1018 that the patient fails to obtain medical attention when it should be needed. Additionally or alternatively, the machine learning model can determine an underlying factor 1020 that the patient cannot travel to a follow-up appointment with the doctor (which in turn results in the patient failing to get medical attention). The reason that the patient cannot travel to the follow-up appointment could be that the patient is no longer comfortable with driving (due to old age) yet is also unlikely to have access to public transportation, in one embodiment. In any event, as a result of the risk factor and/or underlying factor, the machine learning model can determine that the readmission risk level 1016 should be twenty-five percent rather than five percent (as would have been determined in the absence of social information).

Assume that the risk modeling system uses a threshold, of ten percent, for designating the patient as having a high risk of readmission, in one embodiment. In this scenario, inclusion of the social information as an input to the machine learning model results in the patient being designated as a high-risk patient rather than as a low-risk patient in terms of readmission risk. In other words, the machine learning model in effect identifies a false negative, owing to the social information. In response, the healthcare facility can take remedial actions to reduce the readmission risk of the patient, such as suggesting for the patient to arrange a house call with a doctor. Doing so can increase quality of care, reduce incidence of readmissions, and improve patient outcomes, at least in some cases.

It should be noted that in some embodiments, the machine learning model can determine the heightened readmission risk level 1016 even in an absence of any determinations pertaining to the risk factor 1018 and/or underlying factor 1020. In such embodiments, the machine learning model merely predicts the heightened readmission risk level 1016 without further elaboration.

GUI Example A

Figure 14:
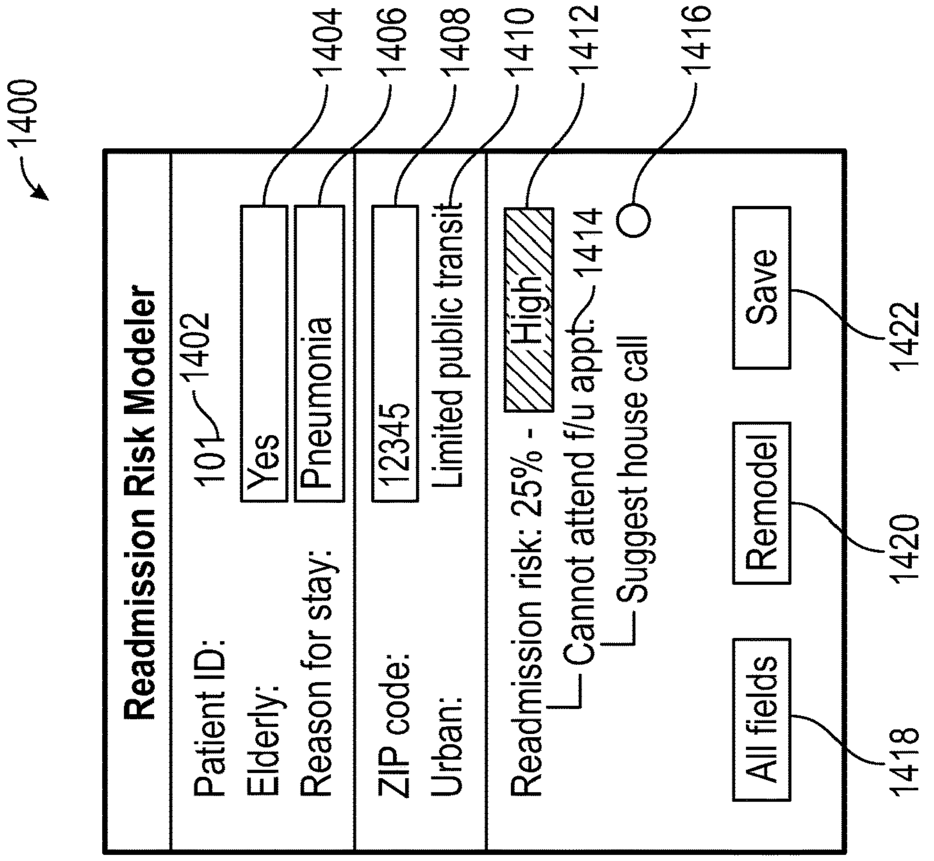

FIGS. 14-17 depict graphical user interfaces (GUIs) that display the readmission risk profiles generated by the risk modeling system, according to some embodiments. Referring forward to FIG. 14, a GUI 1400 is shown as displaying information corresponding to the readmission risk profile of FIG. 10B, according to one embodiment. The GUI 1400 includes a patient identifier 1402, age information 1404 indicating that the patient is elderly, and a reason for stay 1406 indicating that the patient is diagnosed with pneumonia. The GUI 1400 also includes residential information 1408 indicating a ZIP code of the patient. The GUI 1400 further includes social information 1410 corresponding to the residential information 1408. In this example, the social information 1410 is demographic information indicating that the patient resides in a geographic region that has limited availability of public transportation.

The GUI 1400 also includes readmission information such as a readmission risk level 1412 indicating that the patient has a chance of readmission following discharge, of twenty-five percent. In this example, the GUI 1400 also specifies that the readmission risk level 1412 is considered high. That the readmission risk level is considered high is further conveyed via a distinct visual representation, such as a larger font, a different color, and the like, in one embodiment. The readmission information also includes a readmission risk factor 1414 of the patient being unable to attend a follow-up appointment with the doctor. The readmission information further includes remedial information such as a recommended remedial action 1416 of suggesting that the patient arrange a house call with a doctor. The remedial information also includes an indication of whether the remedial action has been performed by the healthcare facility. In this example, the indication denotes that the remedial action has not yet been performed.

In some embodiments, the remedial action can be flagged as having been performed, based on user input received via a computing device of the healthcare facility. For instance, the user input can include clicking on a checkbox via a mouse operatively connected to a desktop or laptop computer, tapping on a touchscreen of a smartphone or tablet, hand gestures detected by a motion-sensing system, and the like. In other embodiments, the remedial action can be flagged, by the risk modeling system without requiring user intervention, as having been performed. For instance, if the remedial action is to send an automated reminder to the patient via a text message, the risk modeling system can flag the remedial action as having been performed, once the automated reminder is sent.

The GUI 1400 also includes a button 1418 to activate display of additional fields of information pertaining to the patient. In addition, the GUI 1400 includes a button 1420 to activate a recalculation of the readmission risk profile by the risk modeling system. Moreover, the GUI 1400 includes a button 1422 to activate saving of any changes to the personal information that have been made via the GUI 1400. Examples of changes include a change to correct a date of birth of a patient, a change to correct a ZIP code of the patient, and a change to a flag indicating whether a remedial action has been performed.

It should be noted that the buttons included in the GUI 1400 and/or functionality associated with the buttons are merely exemplary and do not limit embodiments disclosed herein. Those skilled in the art will recognize that other buttons and/or functionality, such as a button to add new information to the patient information and/or a button to delete existing information from the patient information, are broadly contemplated to be used with disclosed embodiments.

In some embodiments, the extent of recomputation needed can differ based on the nature of changes to the personal information that have been made via the GUI 1400. If the changes pertain to the residential information of the patient (e.g., the ZIP code), the personal information is remapped to the social information based on the changed residential information, and the readmission risk profile is regenerated based on at least the remapped social information. If the changes do not pertain to the residential information of the patient (e.g., changing the date of birth), the readmission risk profile is regenerated based on at least the changed personal information, in one embodiment. If the changes pertain to both residential and non-residential information of the patient, the changed personal information is remapped to the social information based on the changed residential information, and the readmission risk profile is regenerated based on the remapped social information and changed personal information, in one embodiment.

Readmission Risk Profile Example B

Figure 11A:
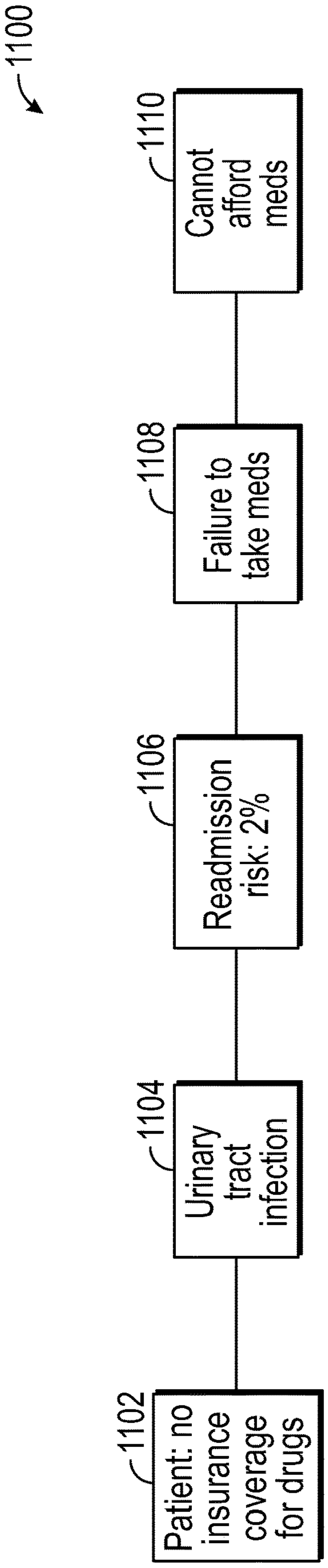
FIGS. 11A-11B illustrate readmission risk profiles generated by the risk modeling system, according to some embodiments.

Referring backward to FIG. 11A, the readmission risk profile 1100 generated for another patient in the absence of social information is shown. The readmission risk profile 1100 is associated with stay information 1102 and medical information 1104 and includes readmission information. The stay information 1102 includes insurance information indicating that the patient does not have insurance coverage for costs associated with prescribed drugs. The medical information 1104 includes a diagnosis of the patient as having a urinary tract infection. The readmission information includes a readmission risk level 1106 that characterizes the patient as having a two-percent risk of being readmitted to the healthcare facility after discharge. The readmission information also includes a readmission risk factor that the patient fails to use prescribed medications. In addition, the readmission information includes an underlying factor indicating that the reason the patient can fail to use prescribed medications is because the patient cannot afford to purchase the prescribed medications.

Figure 11B:
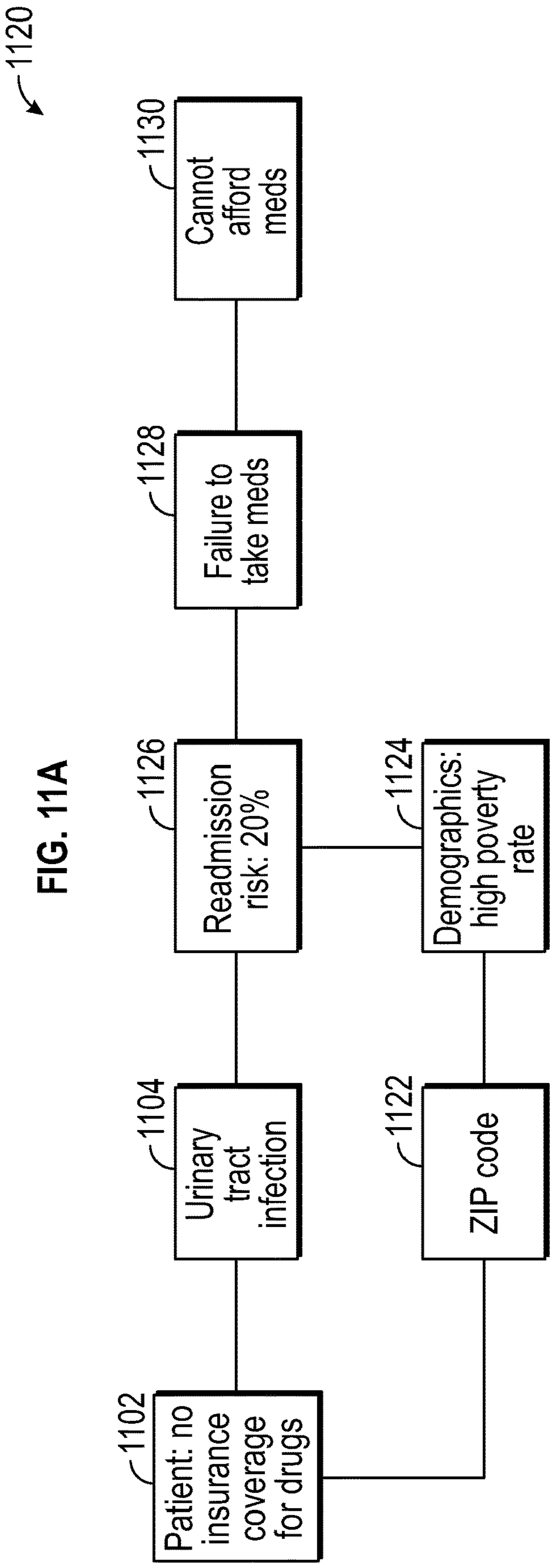

Referring to FIG. 11B, the readmission risk profile 1120 generated for the patient based on social information is shown. The readmission risk profile 1120 is associated with the stay information 1102 and the medical information 1104 and includes readmission risk information. Based on residential information 1122 included in personal information of the patient, the risk modeling system maps patient information of the patient to corresponding social information. As shown, the residential information 1122 includes a ZIP code of the patient. In this example, the social information includes demographic information 1124 indicating that the patient resides in a geographical region having a high poverty rate.

Based on this additional piece of information that is the demographic information 1124, the machine learning model can determine that a readmission risk level 1126 of this patient is heightened as a result of the patient both having no insurance coverage for prescribed drugs and residing in a geographical region that has a high poverty rate. This determination can be made based at least in part on the machine learning model having observed other patients, who lack insurance coverage for prescribed drugs and who reside in geographical regions with high poverty rates, having higher rates of readmission.

Accordingly, the machine learning model can determine a risk factor 1128 that the patient fails to use his prescribed medications. Additionally or alternatively, the machine learning model can determine an underlying factor 1130 that the patient cannot afford to pay for his prescribed medications (which in turn results in the patient failing to use his prescribed medications). The reason that the patient cannot afford to pay for his prescribed medications could be that the patient cannot rely on insurance coverage for the prescribed medications yet is also likely to be in poverty. In any event, as a result of the risk factor and/or underlying factor, the machine learning model can determine that the readmission risk level 1126 should be twenty percent rather than two percent (as would have been determined in the absence of social information).

Assume that the risk modeling system uses the threshold of ten percent for designating the patient as having a high risk of readmission, in one embodiment. In this scenario, inclusion of the social information as an input to the machine learning model results in the patient being designated as a high-risk patient rather than as a low-risk patient in terms of readmission risk. In other words, the machine learning model in effect identifies a false negative, owing to the social information. In response, the healthcare facility can take remedial actions to reduce the readmission risk of the patient, such as suggesting for the patient to be switched to a generic version of the prescribed drug (i.e., if the prescribed drug is a brand-name drug), suggesting a drug assistance program for the patient to join, and so forth.

GUI Example B

Figure 15:
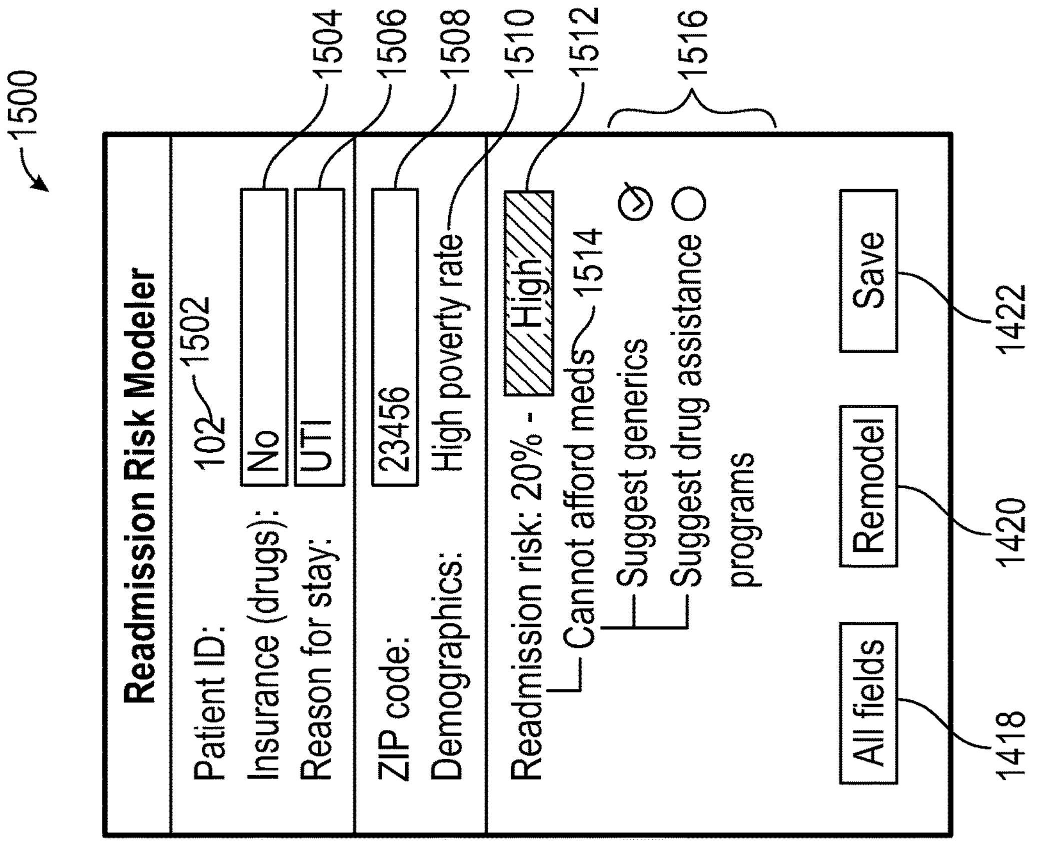
FIGS. 14-17 depict graphical user interfaces that display the readmission risk profiles generated by the risk modeling system, according to some embodiments.

Referring forward to FIG. 15, a GUI 1500 is shown as displaying information corresponding to the readmission risk profile of FIG. 11B, according to one embodiment. The GUI 1500 includes a patient identifier 1502, insurance information 1504 indicating that the patient does not have insurance coverage for prescribed drugs, and a reason for stay 1506 indicating that the patient is diagnosed with a urinary tract infection. The GUI 1500 also includes residential information 1508 indicating a ZIP code of the patient. The GUI 1500 further includes social information 1510 corresponding to the residential information 1508. In this example, the social information 1510 is demographic information indicating that the patient resides in a geographic region that has a high rate of poverty.

The GUI 1500 also includes readmission information such as a readmission risk level 1512 indicating that the patient has a twenty-percent chance of readmission following discharge. In this example, the GUI 1500 also specifies that the readmission risk level 1512 is considered high. The readmission information also includes a readmission risk factor 1514 of the patient being unable to afford prescribed medications. The readmission information further includes remedial information 1516. In some embodiments, the risk modeling system can identify multiple remedial actions intended to address a given risk factor. As shown, the remedial information 1516 includes recommended remedial actions of suggesting for the patient to be switched to the generic version of the prescribed drug and suggesting a drug assistance program for the patient to join. Depending on the embodiment, the remedial actions can be recommended in conjunction or in the alternative.

The remedial information 1516 also includes indications of whether the remedial actions have been performed by the healthcare facility. In this example, the indications denote that a suggestion has been made to the patient and/or the doctor to switch the patient to the generic version of the prescribed drug. On the other hand, the indications denote that no suggestion has yet been made for the patient to join any drug assistance program.

The GUI 1500 also includes the button 1418 to activate display of additional fields of information pertaining to the patient, the button 1420 to activate a recalculation of the readmission risk profile by the risk modeling system, and the button 1422 to activate saving of any changes to the personal information that have been made via the GUI 1500.

Readmission Risk Profile Example C

Figure 12A:
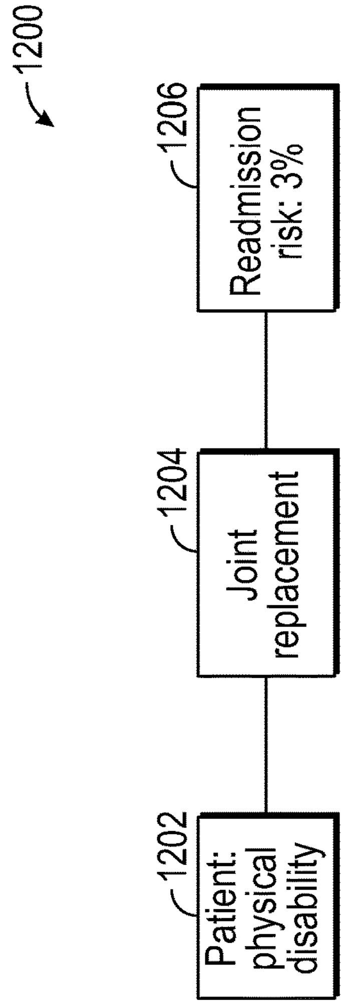
FIGS. 12A-12B illustrate readmission risk profiles generated by the risk modeling system, according to some embodiments.

Referring backward to FIG. 12A, the readmission risk profile 1200 generated for another patient in the absence of social information is shown. The readmission risk profile 1200 is associated with medical information and includes readmission information. The medical information includes an indication 1202 that the patient has a physical disability and an indication 1204 that the patient is prescribed treatment including joint replacement surgery. In this example, the reason for the patient to stay at the healthcare facility is because the patient has undergone a successful joint replacement surgery. The readmission information includes a readmission risk level 1206 that characterizes the patient as having a three-percent risk of being readmitted to the healthcare facility after discharge. In this example, no determinations as to risk factor and underlying factor are made for the patient by the risk modeling system.

Figure 12B:
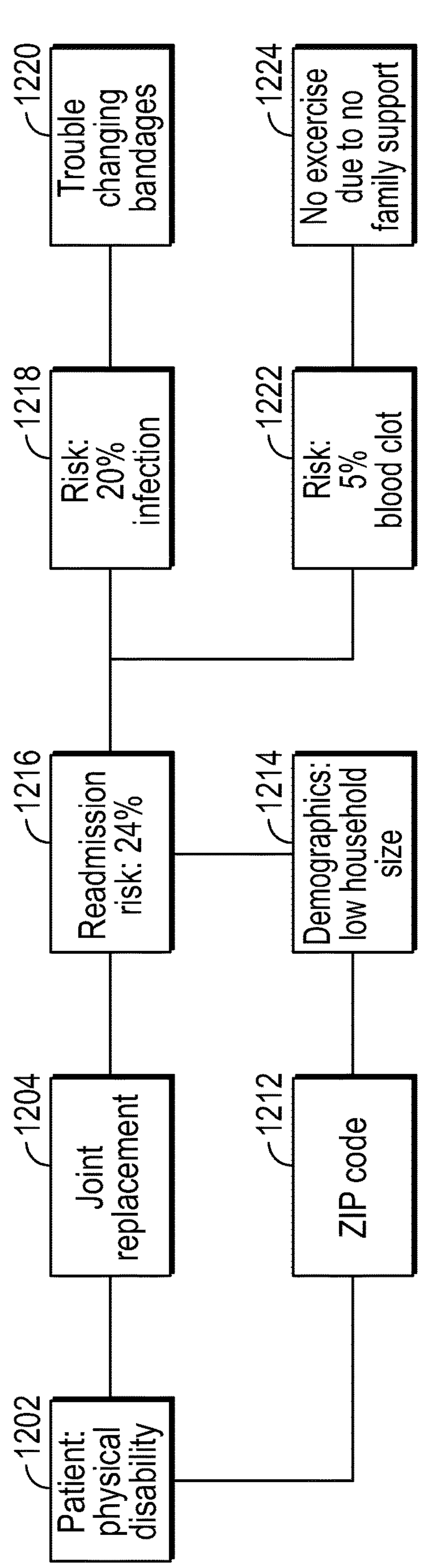

Referring to FIG. 12B, the readmission risk profile 1210 generated for the patient based on social information is shown. The readmission risk profile 1210 is associated with the medical information that includes the indication 1202 that the patient is physically disabled and the indication 1204 that the patient is prescribed joint replacement surgery. Based on residential information 1212 included in personal information of the patient, the risk modeling system maps patient information of the patient to corresponding social information. As shown, the residential information 1212 includes a ZIP code of the patient. In this example, the social information includes demographic information 1214 indicating that the patient resides in a geographical region having a low household size (e.g., median or mode household size).

Based on this additional piece of information that is the demographic information 1214, the machine learning model can determine that a readmission risk level 1216 of this patient is heightened as a result of the patient both having a physical disability and residing in a geographical region having a low household size (where the household size is taken as being indicative of a living arrangement of the patient). This determination can be made based at least in part on the machine learning model having observed other patients, who are physically disabled and reside in geographical regions having low household sizes, having higher rates of readmission.

In some embodiments, the machine learning model can identify multiple risk factors, each with its own risk level, and the machine learning model can also determine an overall risk level based on the risk levels of the multiple risk factors. As shown, the machine learning model can determine a risk factor 1218 that the patient can acquire an infection, in one embodiment. Additionally or alternatively, the machine learning model can determine an underlying factor 1220 that the patient has a twenty-percent chance of becoming infected, because the patient has trouble changing bandages regularly (which in turn results in the patient becoming infected). The reason that the patient can have trouble changing bandages regularly could be that the patient is physically disabled yet is unlikely to be living with family members who can provide assistance, in one embodiment.

As shown, the machine learning model can determine an additional risk factor 1222 that the patient suffers a blood clot, in one embodiment. Additionally or alternatively, the machine learning model can determine an underlying factor 1224 that the patient has a five-percent chance of suffering a blood clot, because the patient fails to exercise.at home (which in turn increases the likelihood of a blood clot following joint replacement surgery). The reason that the patient can fail to exercise could be that the patient is physically disabled yet is unlikely to be living with family members who can provide physical assistance and/or emotional support to motivate the patient to exercise despite the physical disability.

In any event, as a result of the risk factors and/or underlying factors, the machine learning model can determine that the overall risk level 1216 of readmission should be twenty-four percent rather than three percent (as would have been determined in the absence of social information). In this example, the figure of twenty-four percent can be calculated as a likelihood of the patient becoming infected or suffering a blood clot (or both), i.e., 20%+5%−(20%*5%)=24%.

Assume that the risk modeling system uses the threshold of ten percent for designating the patient as having a high risk of readmission, in one embodiment. In this scenario, inclusion of the social information as an input to the machine learning model results in the patient being designated as a high-risk patient rather than as a low-risk patient in terms of readmission risk. In other words, the machine learning model in effect identifies a false negative, owing to the social information. In response, the healthcare facility can take remedial actions to reduce the readmission risk of the patient, such as suggesting for the patient to make appointments with a nurse for a bandage change, providing reminders to the patient by telephone to remind the patient to exercise at home following discharge, and so forth.

GUI Example C

Figure 16:
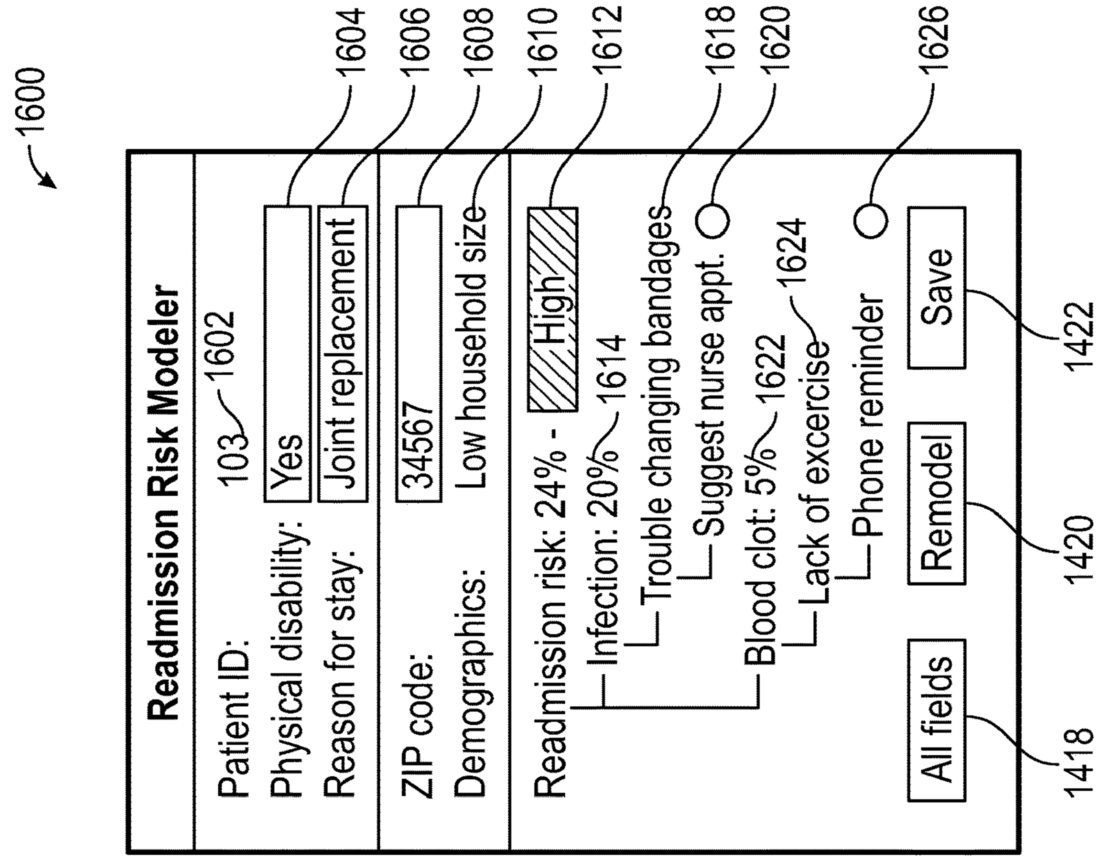

Referring forward to FIG. 16, a GUI 1600 is shown as displaying information corresponding to the readmission risk profile of FIG. 12B, according to one embodiment. The GUI 1600 includes a patient identifier 1602, medical information 1604 indicating that the patient is physically disabled, and a reason for stay 1606 indicating that the patient has undergone joint replacement surgery. The GUI 1600 also includes residential information 1608 indicating a ZIP code of the patient. The GUI 1600 further includes social information 1610 corresponding to the residential information 1608. In this example, the social information 1610 is demographic information indicating that the patient resides in a geographic region that has a low household size.

The GUI 1600 also includes readmission information such as an overall readmission risk level 1612 indicating that the patient has an overall chance of readmission following discharge, of twenty-four percent. In this example, the GUI 1600 also specifies that the overall readmission risk level 1612 is considered high.

The readmission information also includes a readmission risk factor 1614 of the patient becoming infected. As shown, the readmission risk factor 1614 has an associated risk level of twenty percent. The readmission information further includes corresponding remedial information such as a recommended remedial action 1620 to suggest the patient to make an appointment to see a nurse.

Moreover, the readmission information includes an additional readmission risk factor 1622 of the patient suffering a blood clot. As shown, the additional readmission risk factor 1622 has an associated risk level of five percent. The readmission information further includes corresponding remedial information such as a recommended remedial action 1626 to remind the patient by telephone to exercise at home following discharge. The overall readmission risk level 1612 is determined based on the risk levels associated with the readmission risk factors, in one embodiment.

The remedial information also includes indications of whether the remedial actions have been performed by the healthcare facility. In this example, the indications denote that no suggestion has yet been made for the patient to make an appointment to see a nurse. Moreover, the indications denote that no telephone call has yet been placed to remind the patient to exercise at home.

The GUI 1600 also includes the button 1418 to activate display of additional fields of information pertaining to the patient, the button 1420 to activate a recalculation of the readmission risk profile by the risk modeling system, and the button 1422 to activate saving of any changes to the personal information that have been made via the GUI 1600.

Readmission Risk Profile Example D

Figure 13A:
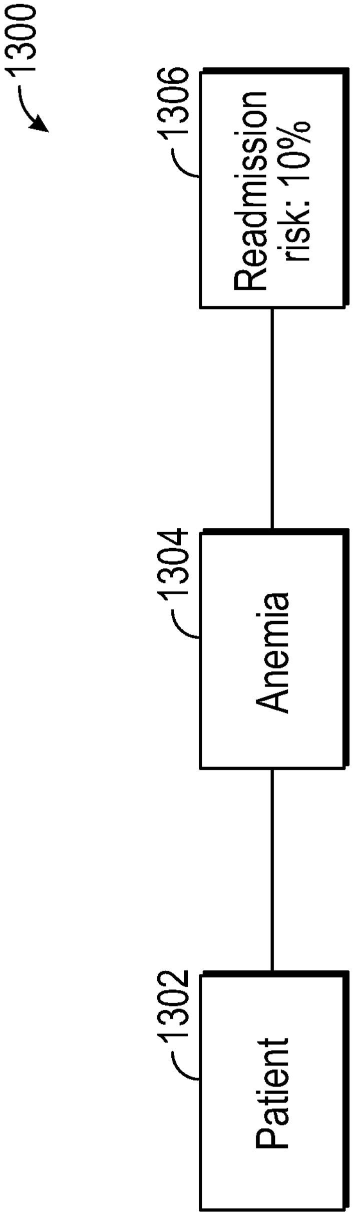
FIGS. 13A-13B illustrate readmission risk profiles generated by the risk modeling system, according to some embodiments.

Referring backward to FIG. 13A, the readmission risk profile 1300 generated for another patient in the absence of social information is shown. The readmission risk profile 1300 is associated with personal information 1302 and medical information 1304 that pertain to the patient. The medical information 1304 indicates that the patient is diagnosed with anemia. Further, the readmission risk profile 1300 includes readmission information such as a readmission risk level 1306. The readmission risk level 1306 characterizes the patient as having a ten-percent risk of being readmitted to the healthcare facility after discharge. In this example, no determinations as to risk factor and underlying factor are made for the patient by the risk modeling system.

Figure 13B:
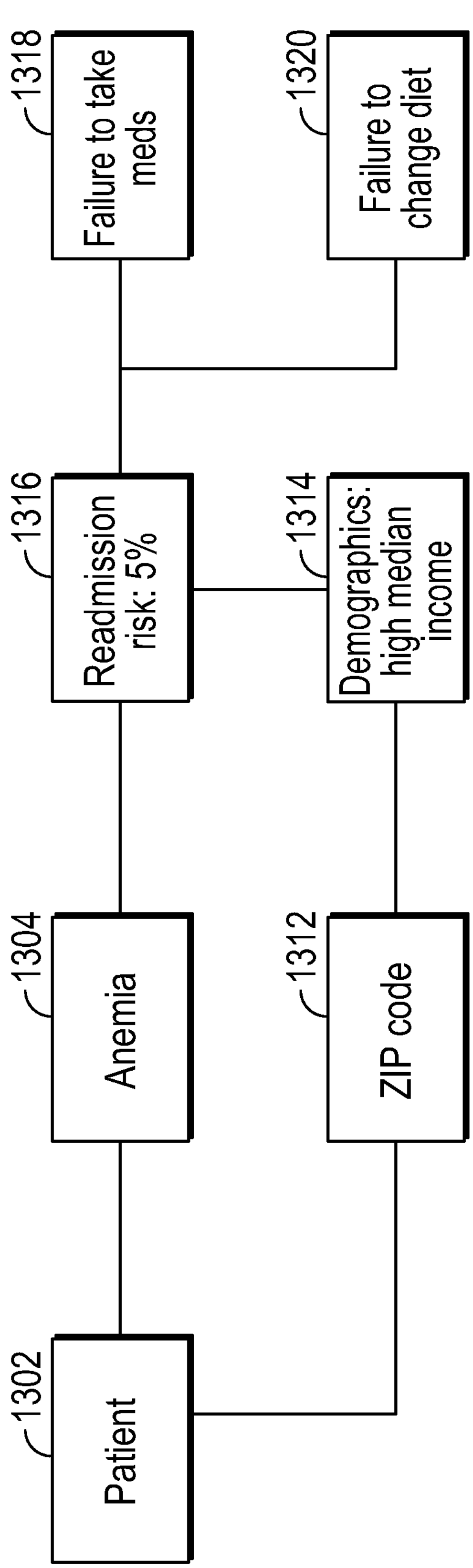

Referring to FIG. 13B, the readmission risk profile 1310 generated for the patient based on social information is shown. The readmission risk profile 1310 is associated with the personal information 1302 and the medical information 1304. Based on residential information 1312 included in the personal information 1302 of the patient, the risk modeling system maps patient information of the patient to corresponding social information. As shown, the residential information 1312 includes a ZIP code of the patient. In this example, the social information includes demographic information 1314 indicating that the patient resides in a geographical region having a high median income (e.g., individual or household income).

Based on this additional piece of information that is the demographic information 1314, the machine learning model can determine that a readmission risk level 1316 of this patient is heightened as a result of the patient residing in a geographical region having a high median income. This determination can be made based at least in part on the machine learning model having observed other patients, who reside in geographical regions having high median incomes, having lower rates of readmission.

In some embodiments, the machine learning model can identify multiple risk factors, where each risk factor does not necessarily have an associated risk level, according to one embodiment. As shown, the machine learning model can determine a risk factor 1318 that the patient fails to use prescribed medications. Additionally or alternatively, the machine learning model can determine a risk factor 1320 that the patient fails to change a diet as the doctor has recommended. The reason that the patient can be more likely to use prescribed medications could be that the income level of the patient is likely high given the high median income and should thus make the patient more likely to be able to afford the prescribed medications. Similarly, the reason that the patient can be more likely to change to a recommended diet could be that the likely high income level of the patient should make the patient more likely to be able to afford types of food specified in the recommended diet (e.g., meat to cure anemia based on iron deficiency, where a meat-based diet can be more expensive than diets based on plants, starches, and/or fats).

In any event, as a result of the risk factors, the machine learning model can determine that the risk level 1316 of readmission should only be five percent rather than ten percent (as would have been determined in the absence of social information). In this example, no underlying factors are determined by the machine learning model, and no remedial actions are determined by the risk modeling system.

Assume that the risk modeling system uses the threshold of ten percent for designating the patient as having a high risk of readmission, in one embodiment. In this scenario, inclusion of the social information as an input to the machine learning model results in the patient being designated as a low-risk patient rather than as a high-risk patient in terms of readmission risk. In other words, the machine learning model in effect eliminates a false positive, owing to the social information. In response, the healthcare facility can refrain from taking remedial actions, because the remedial actions may not be warranted for this patient after all.

GUI Example D

Figure 17:
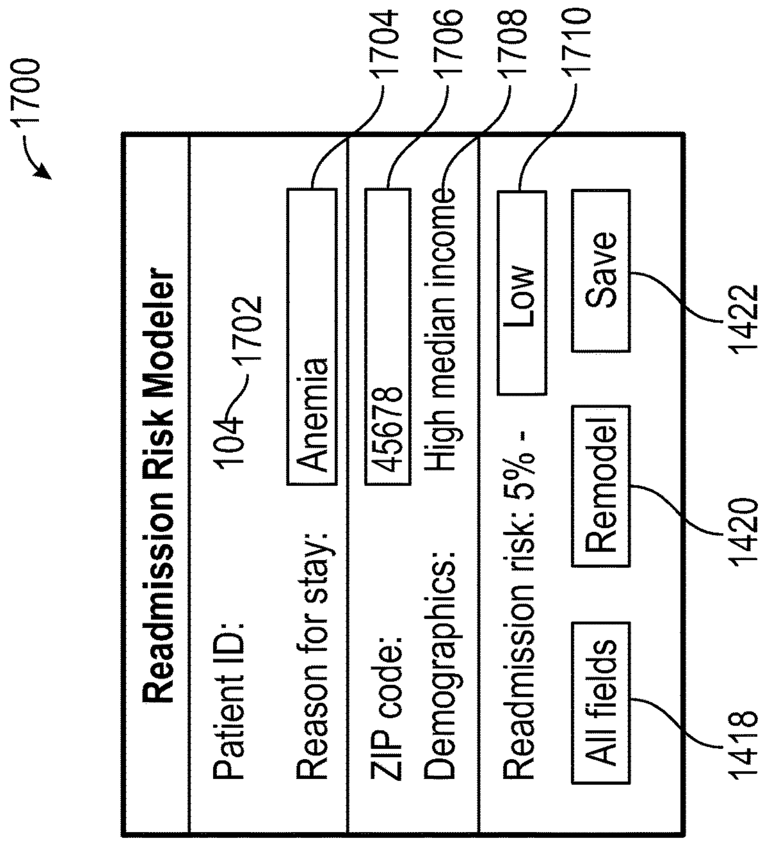

Referring forward to FIG. 17, a GUI 1700 is shown as displaying information corresponding to the readmission risk profile of FIG. 13B, according to one embodiment. The GUI 1700 includes a patient identifier 1702 and a reason for stay 1704 indicating that the patient is diagnosed with anemia. The GUI 1700 also includes residential information 1706 indicating a ZIP code of the patient. The GUI 1700 further includes social information 1708 corresponding to the residential information 1706. In this example, the social information 1708 is demographic information indicating that the patient resides in a geographic region that has a high median income.

The GUI 1700 also includes readmission information such as a readmission risk level 1710 indicating that the patient has only a five-percent chance of readmission following discharge. In this example, the GUI 1700 also specifies that the readmission risk level 1710 is considered low. As shown, however, the GUI 1700 does not include any indication of the determined risk factor that the patient fails to use prescribed medications. The GUI 1700 also does not include any indication of the determined risk factor that the patient fails to change to a recommended diet. In some embodiments, these risk factors are excluded from the GUI 1700 despite having been determined by the risk modeling system, because the readmission risk level 1710 is low. In these embodiments, the GUI 1700 can include an option to toggle display of these risk factors. In other embodiments, however, the GUI 1700 can include or exclude these risk factors for/from display regardless of the readmission risk level 1710.

The GUI 1700 also includes the button 1418 to activate display of additional fields of information pertaining to the patient, the button 1420 to activate a recalculation of the readmission risk profile by the risk modeling system, and the button 1422 to activate saving of any changes to the personal information that have been made via the GUI 1700.

Example Components of a Risk Modeling Application

Figure 18:
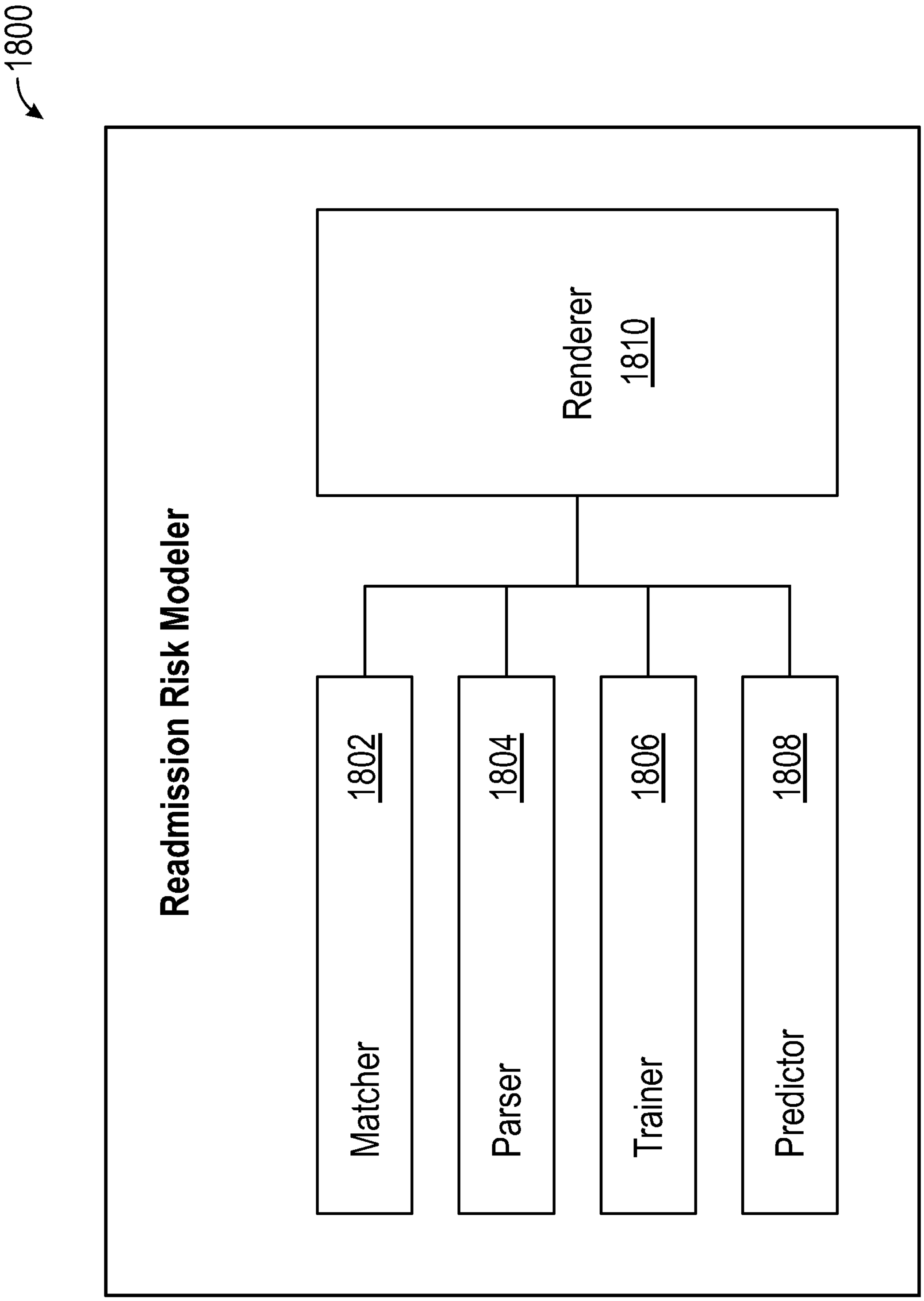
FIG. 18 is a block diagram showing components of a risk modeling application for patient readmissions to the healthcare facility, according to one embodiment.

FIG. 18 is a block diagram showing components of a risk modeling application 1800 for patient readmissions to the healthcare facility, according to one embodiment. The risk modeling application 1800 can be any application executed by the risk modeling system to provide the risk modeling functionality described herein. The risk modeling application 1800 is also referred to as a readmission risk modeler. As shown, the components include a matcher 1802, a parser 1804, a trainer 1806, a predictor 1808, and a renderer 1810.

In one embodiment, the matcher 1802 matches patient information with social information from the social database. Additionally or alternatively, the matcher 1802 matches readmission risk profiles with remedial actions from the remedial database and/or performs additional matching operations described herein. The parser 1804 performs parsing operations, such as for the preprocessing and/or processing operations described herein. The parsing operations can be performed on the patient information, social information and/or remedial information. Doing so produces information that is in a format more suitable for use by the machine learning model and/or the risk modeling application 1800.

The trainer 1806 trains the machine learning model to predict readmission risk profiles of patients based on at least the social information, in one embodiment. The predictor 1808 applies the trained machine learning model to predict the readmission risk profiles of the patients. The renderer 1810 generates indications of the readmission risk profiles. In some embodiments, the renderer 1810 also generates GUIs that include at least the indications of the readmission risk profiles. Depending on the embodiment, the functionality of the components can be divided among a greater or lesser number of components than shown.

Example Method for Augmenting Patient Information with Social Information

Figure 19:
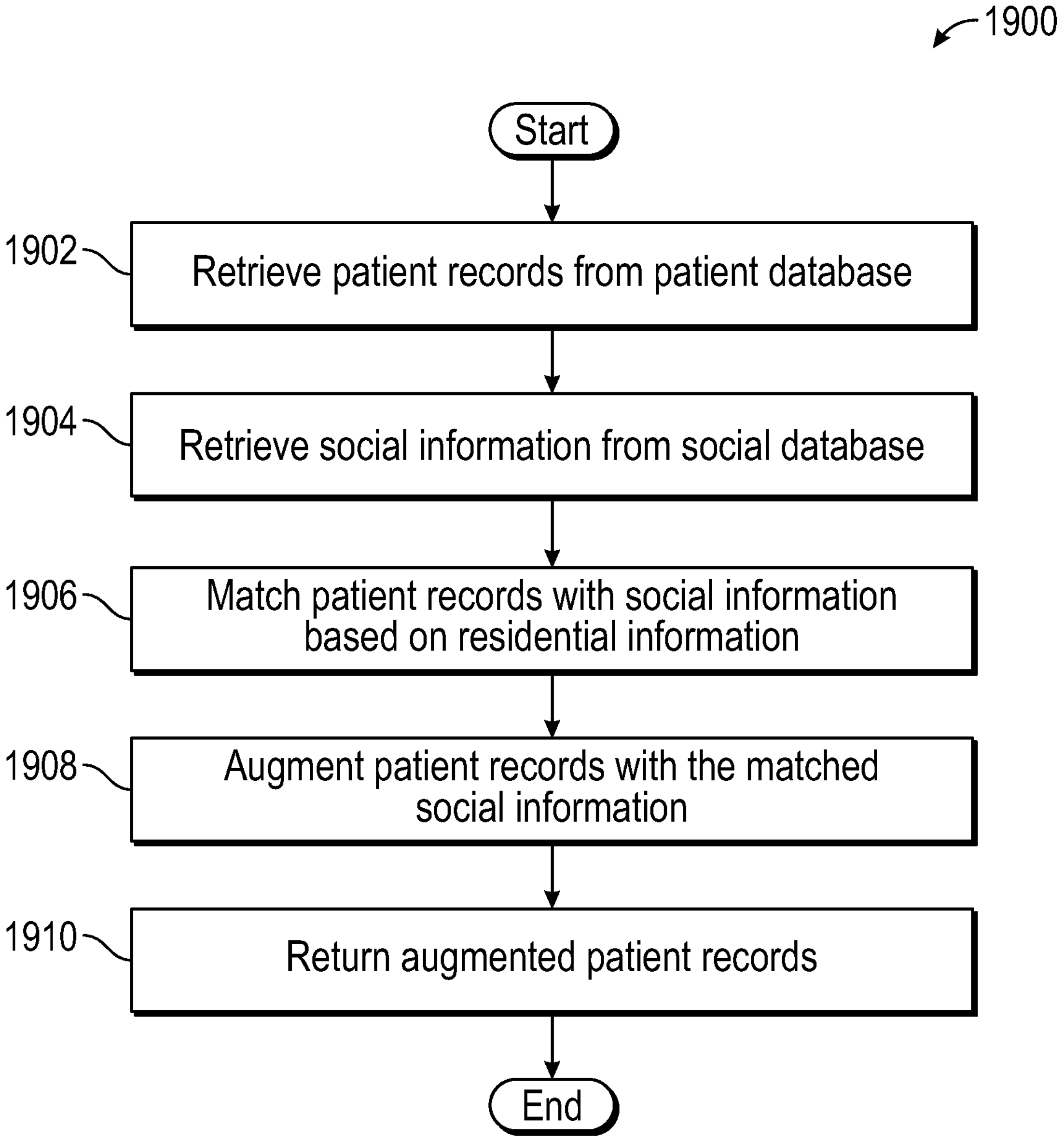
FIG. 19 is a flowchart for matching patient information with social information based on residence information included in personal information, according to one embodiment.

FIG. 19 is a flowchart depicting a method 1900 for matching patient information with social information based on residence information included in personal information, according to one embodiment. As shown, the method 1900 begins at step 1902, where the risk modeling system retrieves patient records from the patient database. At step 1904, the risk modeling system retrieves social information from a social database. At step 1906, the risk modeling system matches the patient records with the social information based on residential information. At step 1908, the risk modeling system augments the patient records with the matched social information. At step 1910, the risk modeling system returns the augmented patient records. Depending on the embodiment, the augmented patient records can be stored in the patient database or reassembled on demand. After the step 1910, the method 1900 ends. At least in some embodiments, the steps of the method 1900 are further described above in conjunction with the block diagram 300 of FIG. 3.

Example Method for Training Machine Learning Models

Figure 20:
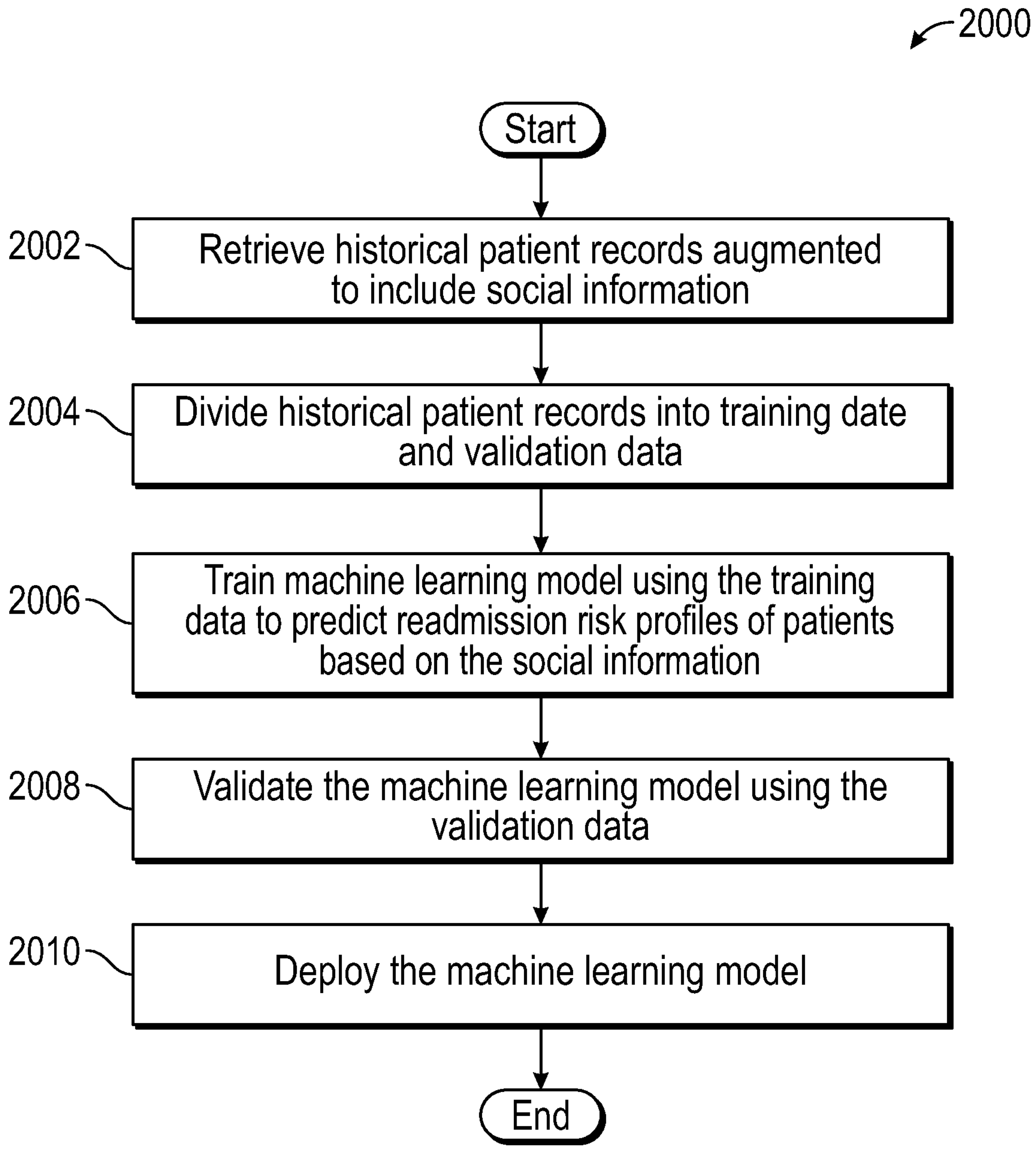
FIG. 20 is a flowchart for training the risk modeling system for patient readmissions to the healthcare facility, according to one embodiment.

FIG. 20 is a flowchart depicting a method 2000 for training the risk modeling system for patient readmissions to the healthcare facility, according to one embodiment. As shown, the method 2000 begins at step 2002, where the risk modeling system retrieves historical patient records augmented to include corresponding social information. At step 2004, the risk modeling system divides the historical patient records into training data and validation data. At step 2006, the risk modeling system trains a machine learning model to predict readmission risk profiles of patients based on at least the social information. At step 2008, the risk modeling system validates the machine learning model using the validation data. Assuming validation is successful, then at step 2010, the risk modeling system deploys the machine learning model. In some embodiments, if validation is unsuccessful, the method 2000 returns to the step 2006 to further train the machine learning model. After the step 2010, the method 2000 ends. At least in some embodiments, the steps of the method 2000 are further described above in conjunction with the risk modeling system 100 of FIG. 1A.

Example Method for Applying Machine Learning Models

Figure 21:
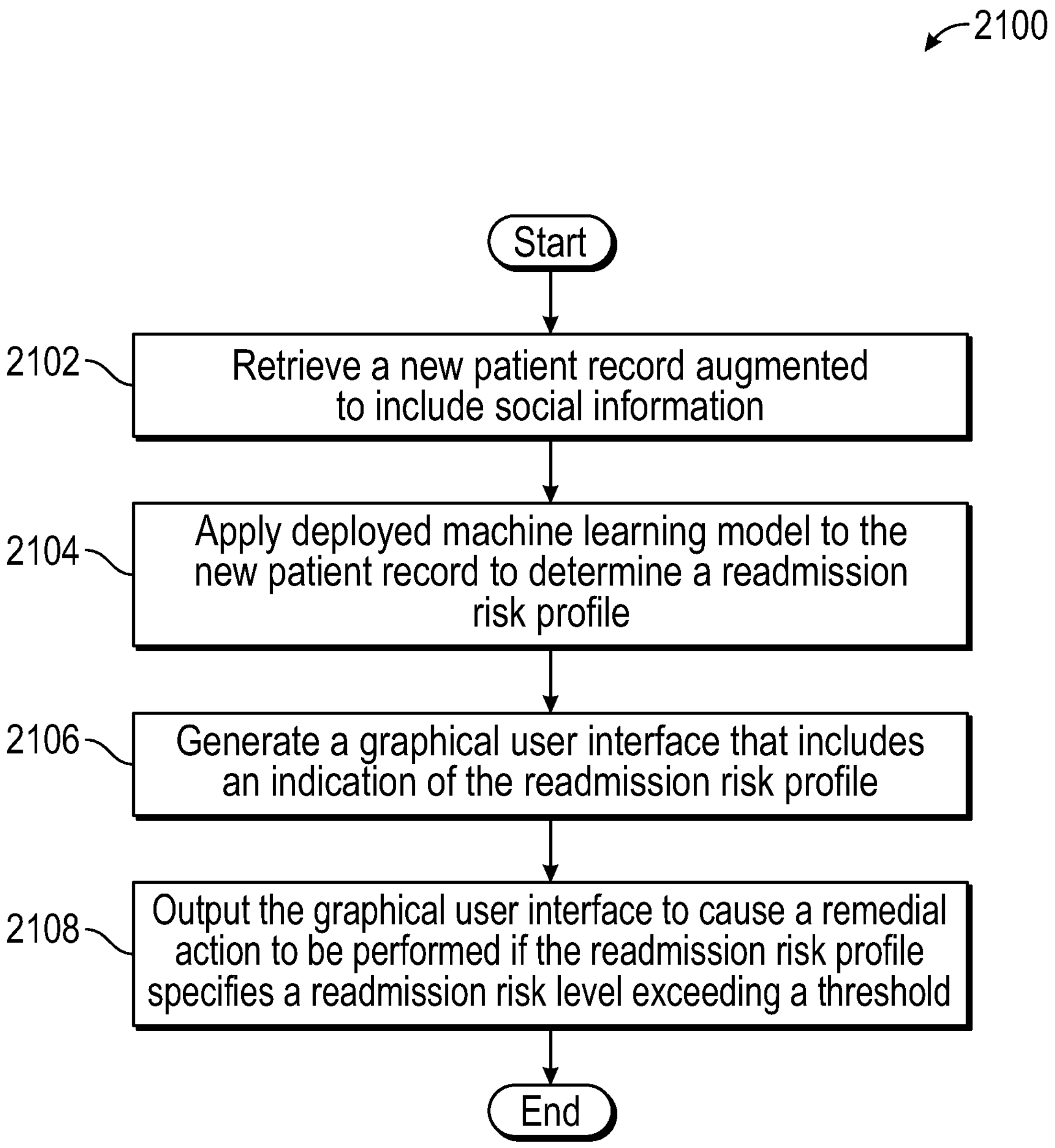
FIG. 21 is a flowchart for applying the risk modeling system for patient readmissions to the healthcare facility, according to one embodiment.

FIG. 21 is a flowchart depicting a method 2100 for applying the risk modeling system for patient readmissions to the healthcare facility, according to one embodiment. As shown, the method 2100 begins at step 2102, where the risk modeling system retrieves a new patient record augmented to include corresponding social information. At step 2104, the risk modeling system applies the deployed machine learning model to the new patient record to determine a readmission risk profile of the patient reflected in the new patient record. At step 2106, the risk modeling system generates a GUI that includes an indication of the readmission risk profile. At step 2108, the risk modeling system outputs the GUI to cause a remedial action to be performed if the readmission risk profile specifies a readmission risk level exceeding a threshold. After the step 2108, the method 2100 ends. At least in some embodiments, the steps of the method 2100 are further described above in conjunction with the risk modeling system 150 of FIG. 1B.

Example Method to Preprocess Unstructured Data to Improve Machine Learning

Figure 22:
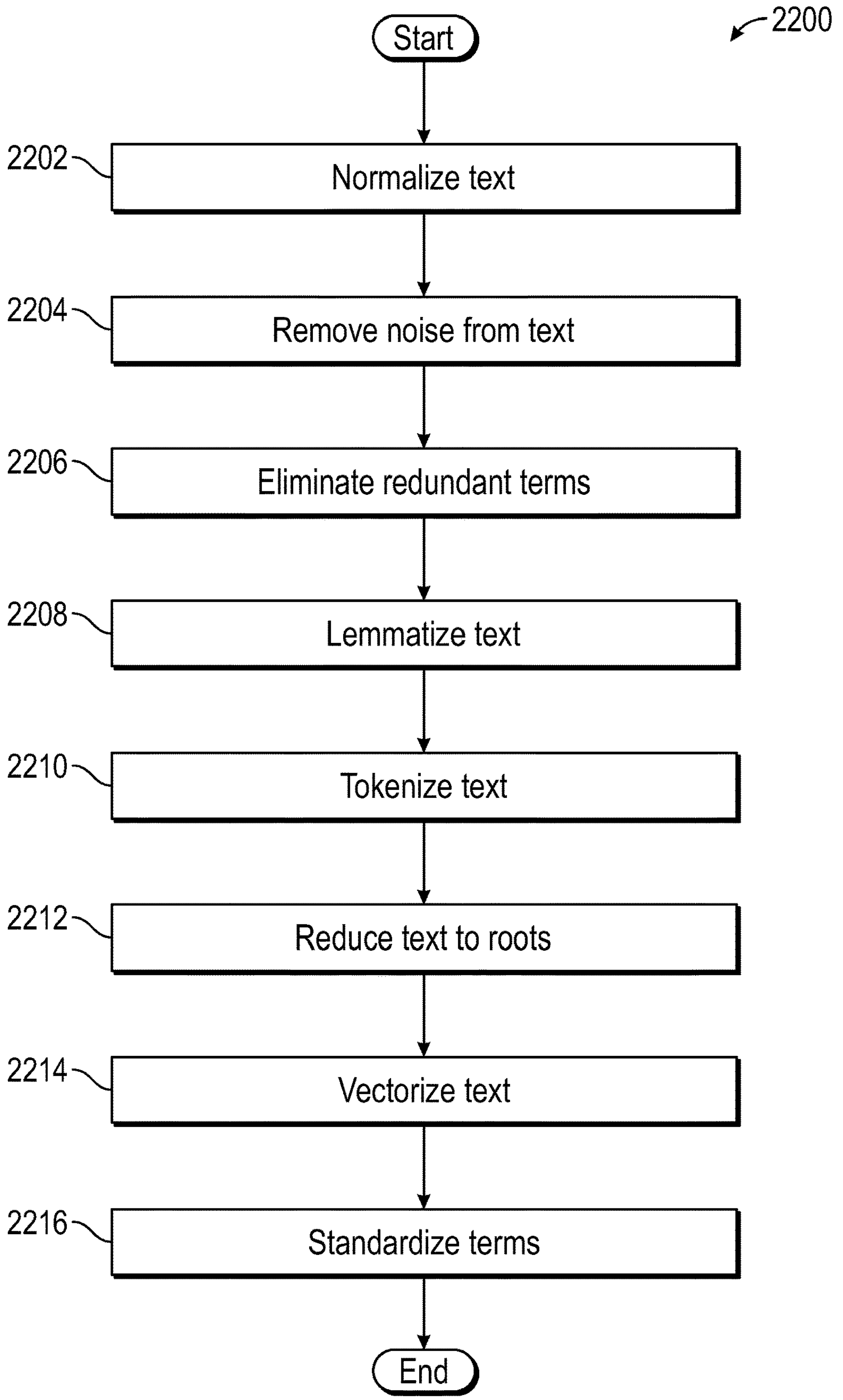
FIG. 22 is a flowchart for preprocessing unstructured input data to improve machine learning results, according to one embodiment.

FIG. 22 is a flow diagram depicting a method 2200 for preprocessing unstructured input data for improved machine learning, according to one embodiment. At least in some embodiments, the method 2200 corresponds to the workflow 200 of FIG. 2. As shown, the method 2200 begins at step 2202, where the risk modeling system normalizes the extracted natural language text, according to one embodiment. As discussed above in conjunction with FIG. 2, this normalization can include a wide variety of text normalization processes, such as converting all characters in the extracted text to lowercase or converting accented characters to unaccented characters.

At step 2204, the risk modeling system removes noise from the text, according to one embodiment. As discussed above, noise removal can include identification and removal of portions of the extracted text that do not carry meaningful or probative value, such as extra white or blank spaces. At step 2206, the risk modeling system eliminates redundant elements or terms from the text, according to one embodiment. As discussed above, this step can include eliminating verbs, conjunctions, or other extraneous words, that do not aid the machine learning task.

At step 2208, the risk modeling system lemmatizes the text, according to one embodiment. As discussed above, text lemmatization can include converting words from their inflectional or other form to a base form, such as replacing "holding," "holds," and "held" with the base form "hold." At step 2210, the risk modeling system tokenizes the text, according to one embodiment. As discussed above, tokenizing the text can include tokenizing a paragraph into a set of sentences.

At step 2212, the risk modeling system reduces the text to one or more roots, according to one embodiment. As discussed above, the root generation can include reducing a phrase to its most relevant bigram for downstream operations involving training or applying the machine learning model. At step 2214, the risk modeling system vectorizes the text, according to one embodiment. As discussed above, vectorization can include generating word embedding vectors.

At step 2216, the risk modeling system standardizes terms in the text, according to one embodiment. As discussed above, the standardization can use natural language processing to identify derivatives of medical diagnoses and/or treatments in the patient information. After the step 2216, the method 2200 ends. At least in some cases, the steps of the method 2200 can improve results of the natural language processing algorithm and, hence, increase the processing efficiency and/or prediction accuracy of the machine learning model.

Advantageously, embodiments presented in this disclosure provide a risk modeling system that applies machine learning to predict whether a patient is at risk of readmission to a healthcare facility after discharge. To that end, the risk modeling system maps patient information to social information from one or more social data sources. The mapping is performed based on residential information included in the patient information. The social information includes at least one of demographic information and urban information. The risk modeling system uses the patient information and social information to predict whether the patient is at risk of readmission to the healthcare facility. By taking the social information into account, the risk modeling system can generate predictions that, at least in some cases, have a greater measure of accuracy at least relative to predictions that do not take the social information is not taken into account. At least in such instances, the risk modeling system achieves the technical advantage of increasing prediction accuracy of machine learning models, thereby improving the technical field of machine learning to predict patient risks.

Furthermore, the risk modeling system can map the readmission risk profile to corresponding remedial actions. These remedial actions can be taken to reduce the risk of patient readmission. In certain embodiments, these remedial actions can include treatment plans involving administering additional or modified medical treatments to the patient, thereby causing a particular treatment or prophylaxis to be effected for preventing or reducing an incidence or extent of illness or injury of patients following discharge from a healthcare facility. In this way, embodiments presented in this disclosure lower patient readmission rates and improve quality of care and patient outcomes of healthcare facilities.

Example Computing Hardware

Figure 23:
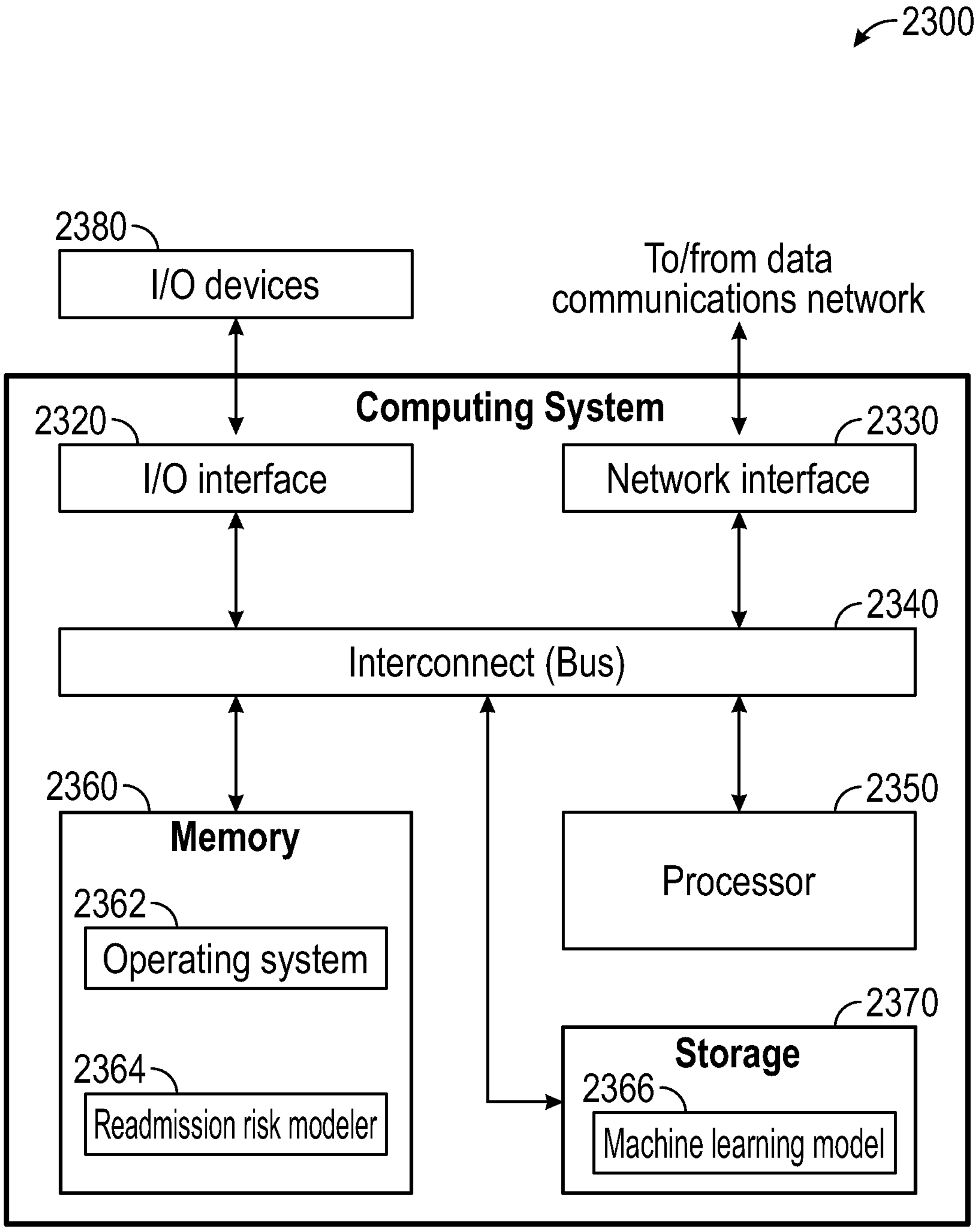
FIG. 23 is a block diagram of a computing system to model risk of patient readmissions to the healthcare facility, according to one embodiment.

FIG. 23 illustrates a computing system 2300, which can be used to implement the risk modeling system 100 of FIG. 1A, the risk modeling system 150 of FIG. 1B, or any other system described in the present disclosure. In this regard, the computing system 2300 can include a computer, a laptop, a tablet, a smartphone, web server, data center, cloud computing environment, etc. As shown, the computing system 2300 includes, without limitation, a computer processor 2350 (e.g., a central processing unit), a network interface 2330, and memory 2360. The computing system 2300 can also include an input/output (I/O) device interface 2320 connecting I/O devices 2380 (e.g., keyboard, display and mouse devices) to the computing system 2300.

The processor 2350 retrieves and executes programming instructions stored in the memory 2360 (e.g., a non-transitory computer-readable medium). Similarly, the processor 2350 stores and retrieves application data residing in the memory 2360. An interconnect 2340 facilitates transmission, such as of programming instructions and application data, between the processor 2350, I/O device interface 2320, storage 2370, network interface 2330, and memory 2360. The processor 2350 is included to be representative of a single processor, multiple processors, a single processor having multiple processing cores, and the like.

The memory 2360 and the storage 2370 are generally included to be representative of volatile and non-volatile memory elements. For example, the memory 2360 and the storage 2370 can include random access memory and a disk drive storage device. Although shown as a single unit, the memory 2360 or the storage 2370 can be a combination of fixed and/or removable storage devices, such as magnetic disk drives, flash drives, removable memory cards or optical storage, network attached storage (NAS), or a storage area-network (SAN). The storage 2370 can include both local storage devices and remote storage devices accessible via the network interface 2330.

One or more components, of FIG. 18, of the risk modeling application 2364 can be maintained in the memory 2360 to perform the functionality of the matcher, parser, trainer, predictor, and/or renderer as described herein. Further, one or more machine learning models 2366 can be maintained in the storage 2370 to predict the readmission risk profile of a patient admitted to a healthcare facility.

Further, the computing system 2300 is included to be representative of a physical computing system as well as virtual machine instances hosted on a set of underlying physical computing systems. Further still, although shown as a single computing device, one of ordinary skill in the art will recognize that the components of the computing system 2300 can be distributed across multiple computing systems operatively connected by a data communications network.

As shown, the memory 2360 includes an operating system 2362. The operating system 2362 can facilitate receiving input from and providing output to various components. For example, the network interface 2330 can be used to output the GUIs described herein. In another example, the network interface 2330 can be used to receive historical patient records for training the machine learning model as described herein. Additionally or alternatively, the network interface 2330 can be used to receive social information and remedial information from the social database and remedial database, respectively.

ADDITIONAL CONSIDERATIONS

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

Clause 1: A method comprising receiving a patient record for a patient admitted to a healthcare facility, the patient record including social information determined for the patient; applying a machine learning model to the patient record to predict a readmission risk profile of the patient; and outputting an indication of the readmission risk profile of the patient.

Clause 2: In addition to the clause 1, wherein the method further comprises receiving a plurality of patient records of patients previously discharged from the healthcare facility, the plurality of patient records including social information and readmission information; training the machine learning model using training data comprising a first subset of the plurality of patient records; and validating the machine learning model using validation data comprising a second subset of the plurality of patient records.

Clause 3: In addition to the clauses 1 or 2, wherein the method further comprises determining that the readmission risk profile indicates that the patient has a readmission risk level exceeding a threshold; determining one or more remedial actions to be taken for the patient prior to discharging the patient from the healthcare facility, to reduce the readmission risk level of the patient; and outputting an indication of the one or more remedial actions.

Clause 4: In addition to the clauses 1, 2, or 3, wherein the method further comprises receiving a plurality of social records from one or more social data sources; determining the social information for the patient by mapping the patient record to the plurality of social records based on residential information included in the patient record, wherein the social information includes at least one of demographic information or urban information; and augmenting the patient record to include the social information determined for the patient.

Clause 5: In addition to the clauses 1, 2, 3, or 4, wherein the readmission risk profile includes at least one of a readmission risk level or a readmission risk factor determined for the patient.

Clause 6: In addition to the clauses 1, 2, 3, 4, or 5, wherein determining the readmission risk profile comprises predicting, for the patient, a plurality of risk levels including a respective risk level of each of a plurality of readmission risk factors; and determining the readmission risk level based on the based on the plurality of risk levels.

Clause 7: In addition to the clauses 1, 2, 3, 4, 5, or 6, wherein the method further comprises parsing the patient record by tokenizing the text in the patient record and normalizing the tokenized text, converting the tokenized text into an object that is represented numerically using at least one of one-hot encodings or word embedding vectors, and processing the object using a natural language processing algorithm.

Clause 8: A non-transitory computer-readable medium containing instructions executable to perform an operation comprising receiving a patient record for a patient admitted to a healthcare facility, the patient record including social information determined for the patient; applying a machine learning model to the patient record to predict a readmission risk profile of the patient; and outputting an indication of the readmission risk profile of the patient.

Clause 9: In addition to the clause 8, wherein the operation further comprises receiving a plurality of patient records of patients previously discharged from the healthcare facility, the plurality of patient records including social information and readmission information; training the machine learning model using training data comprising a first subset of the plurality of patient records; and validating the machine learning model using validation data comprising a second subset of the plurality of patient records.

Clause 10: In addition to the clause 8 or 9, wherein the operation further comprises determining that the readmission risk profile indicates that the patient has a readmission risk level exceeding a threshold; determining one or more remedial actions to be taken for the patient prior to discharging the patient from the healthcare facility, to reduce the readmission risk level of the patient; and outputting an indication of the one or more remedial actions.

Clause 11: In addition to the clauses 8, 9, or 10, wherein the operation further comprises determining the social information for the patient by mapping the patient record to the plurality of social records based on residential information included in the patient record, wherein the social information includes at least one of demographic information or urban information; and augmenting the patient record to include the social information determined for the patient.

Clause 12: In addition to the clauses 8, 9, 10, or 11, wherein the readmission risk profile includes at least one of a readmission risk level or a readmission risk factor determined for the patient.

Clause 13: In addition to the clauses 8, 9, 10, 11, or 12, wherein determining the readmission risk profile comprises predicting, for the patient, a plurality of risk levels including a respective risk level of each of a plurality of readmission risk factors; and determining the readmission risk level based on the based on the plurality of risk levels.

Clause 14: A system comprising one or more computer processors and a memory containing a program executable by the one or more computer processors to perform an operation comprising receiving a patient record for a patient admitted to a healthcare facility, the patient record including social information determined for the patient; applying a machine learning model to the patient record to predict a readmission risk profile of the patient; and outputting an indication of the readmission risk profile of the patient.

Clause 15: In addition to the clause 14, wherein the operation further comprises receiving a plurality of patient records of patients previously discharged from the healthcare facility, the plurality of patient records including social information and readmission information; training the machine learning model using training data comprising a first subset of the plurality of patient records; and validating the machine learning model using validation data comprising a second subset of the plurality of patient records.

Clause 16: In addition to the clause 14 or 15, wherein the operation further comprises determining that the readmission risk profile indicates that the patient has a readmission risk level exceeding a threshold; determining one or more remedial actions to be taken for the patient prior to discharging the patient from the healthcare facility, to reduce the readmission risk level of the patient; and outputting an indication of the one or more remedial actions.

Clause 17: In addition to the clauses 14, 15, or 16, wherein the operation further comprises receiving a plurality of social records from one or more social data sources; determining the social information for the patient by mapping the patient record to the plurality of social records based on residential information included in the patient record, wherein the social information includes at least one of demographic information or urban information; and augmenting the patient record to include the social information determined for the patient.

Clause 18: In addition to the clauses 14, 15, 16, or 17, wherein the readmission risk profile includes at least one of a readmission risk level or a readmission risk factor determined for the patient.

Clause 19: In addition to the clauses 14, 15, 16, 17, or 18, wherein determining the readmission risk profile comprises predicting, for the patient, a plurality of risk levels including a respective risk level of each of a plurality of readmission risk factors; and determining the readmission risk level based on the based on the plurality of risk levels.

Clause 20: In addition to the clauses 14, 15, 16, 17, 18, or 19, wherein the operation further comprises parsing the patient record by tokenizing the text in the patient record and normalizing the tokenized text; converting the tokenized text into an object that is represented numerically using at least one of one-hot encodings or word embedding vectors; and processing the object using a natural language processing algorithm.

What is claimed is:

1. A method comprising:

receiving a patient record for a patient admitted to a healthcare facility, the patient record including social information determined for the patient, wherein the social information comprises (i) a climate of a geographical region of the patient, (ii) an elevation of the geographical region, (iii) an air quality of the geographical region, (iv) a water quality of the geographical region, and (v) a crime rate of the geographical region;

applying a first machine learning model to the patient record to predict a readmission risk profile of the patient;

determining, based on the readmission risk profile, at least one risk factor and at least one underlying factor indicating a reason for the at least one risk factor;

outputting an indication of the readmission risk profile of the patient via a graphical user interface;

determining, based on processing the readmission risk profile using a second machine learning model, one or more remedial actions to be taken for the patient, prior to discharging the patient from the healthcare facility, to reduce a readmission risk level of the patient, wherein the one or more remedial actions comprise providing modified or additional medical treatments or services to the patient; and in response to determining that the one or more remedial actions have been performed, outputting an indication via the graphical user interface flagging that the one or more remedial actions have been performed.

2. The method of claim 1, further comprising:

receiving a plurality of patient records of patients previously discharged from the healthcare facility, the plurality of patient records including social information and readmission information;

training the first machine learning model using training data comprising a first subset of the plurality of patient records; and validating the first machine learning model using validation data comprising a second subset of the plurality of patient records.

3. The method of claim 1, further comprising:

determining that the readmission risk profile indicates that the readmission risk level of the patient exceeds a threshold; and outputting an indication of the one or more remedial actions.

4. The method of claim 1, further comprising:

receiving a plurality of social records from one or more social data sources;

determining the social information for the patient by mapping the patient record to the plurality of social records based on residential information included in the patient record, wherein the social information includes a size of an economy in the geographical region, a measure of economic growth of the geographical region, a measure of availability of health services in the geographical region, a measure of availability of transportation services in the geographical region, and availability of social support services in the geographical region; and augmenting the patient record to include the social information determined for the patient.

5. The method of claim 1, wherein the readmission risk profile includes a categorical readmission risk level determined for the patient.

6. The method of claim 1, wherein determining the readmission risk profile comprises:

predicting, for the patient, a plurality of risk levels including a respective risk level of each of a plurality of readmission risk factors; and determining the readmission risk level based on the plurality of risk levels.

7. The method of claim 1, further comprising parsing the patient record by:

tokenizing text in the patient record and normalizing the tokenized text;

converting the tokenized text into an object that is represented numerically using at least one of one-hot encodings or word embedding vectors; and processing the object using a natural language processing algorithm.

8. A non-transitory computer-readable medium containing instructions executable to perform an operation comprising:

receiving a patient record for a patient admitted to a healthcare facility, the patient record including social information determined for the patient, wherein the social information comprises (i) a climate of a geographical region of the patient, (ii) an elevation of the geographical region, (iii) an air quality of the geographical region, (iv) a water quality of the geographical region, and (v) a crime rate of the geographical region;

applying a first machine learning model to the patient record to predict a readmission risk profile of the patient;

determining, based on the readmission risk profile, at least one risk factor and at least one underlying factor indicating a reason for the at least one risk factor;

outputting an indication of the readmission risk profile of the patient via a graphical user interface;

determining, based on processing the readmission risk profile using a second machine learning model, one or more remedial actions to be taken for the patient, prior to discharging the patient from the healthcare facility, to reduce a readmission risk level of the patient, wherein the one or more remedial actions comprise providing modified or additional medical treatments or services to the patient; and in response to determining that the one or more remedial actions have been performed, outputting an indication via the graphical user interface flagging that the one or more remedial actions have been performed.

9. The non-transitory computer-readable medium of claim 8, wherein the operation further comprises:

receiving a plurality of patient records of patients previously discharged from the healthcare facility, the plurality of patient records including social information and readmission information;

training the first machine learning model using training data comprising a first subset of the plurality of patient records; and validating the first machine learning model using validation data comprising a second subset of the plurality of patient records.

10. The non-transitory computer-readable medium of claim 8, wherein the operation further comprises:

determining that the readmission risk profile indicates that the readmission risk level of the patient exceeds a threshold; and outputting an indication of the one or more remedial actions.

11. The non-transitory computer-readable medium of claim 8, wherein the operation further comprises:

determining the social information for the patient by mapping the patient record to a plurality of social records based on residential information included in the patient record, wherein the social information includes a size of an economy in the geographical region, a measure of economic growth of the geographical region, a measure of availability of health services in the geographical region, a measure of availability of transportation services in the geographical region, and availability of social support services in the geographical region; and augmenting the patient record to include the social information determined for the patient.

12. The non-transitory computer-readable medium of claim 8, wherein the readmission risk profile includes a categorical readmission risk level determined for the patient.

13. The non-transitory computer-readable medium of claim 9, wherein determining the readmission risk profile comprises:

predicting, for the patient, a plurality of risk levels including a respective risk level of each of a plurality of readmission risk factors; and determining the readmission risk level based on the plurality of risk levels.

14. A system comprising:

one or more computer processors; and a memory containing a program executable by the one or more computer processors to perform an operation comprising:

receiving a patient record for a patient admitted to a healthcare facility, the patient record including social information determined for the patient, wherein the social information comprises (i) a climate of a geographical region of the patient, (ii) an elevation of the geographical region, (iii) an air quality of the geographical region, (iv) a water quality of the geographical region, and (v) a crime rate of the geographical region;

applying a first machine learning model to the patient record to predict a readmission risk profile of the patient;

determining, based on the readmission risk profile, at least one risk factor and at least one underlying factor indicating a reason for the at least one risk factor;

outputting an indication of the readmission risk profile of the patient via a graphical user interface;

determining, based on processing the readmission risk profile using a second machine learning model, one or more remedial actions to be taken for the patient, prior to discharging the patient from the healthcare facility, to reduce a readmission risk level of the patient, wherein the one or more remedial actions comprise providing modified or additional medical treatments or services to the patient; and in response to determining that the one or more remedial actions have been performed, outputting an indication via the graphical user interface flagging that the one or more remedial actions have been performed.

15. The system of claim 14, wherein the operation further comprises:

receiving a plurality of patient records of patients previously discharged from the healthcare facility, the plurality of patient records including social information and readmission information;

training the first machine learning model using training data comprising a first subset of the plurality of patient records; and validating the first machine learning model using validation data comprising a second subset of the plurality of patient records.

16. The system of claim 14, wherein the operation further comprises:

determining that the readmission risk profile indicates that the readmission risk level of the patient exceeds a threshold; and outputting an indication of the one or more remedial actions.

17. The system of claim 14, wherein the operation further comprises:

receiving a plurality of social records from one or more social data sources;

determining the social information for the patient by mapping the patient record to the plurality of social records based on residential information included in the patient record, wherein the social information includes a size of an economy in the geographical region, a measure of economic growth of the geographical region, a measure of availability of health services in the geographical region, a measure of availability of transportation services in the geographical region, and availability of social support services in the geographical region; and augmenting the patient record to include the social information determined for the patient.

18. The system of claim 14, wherein the readmission risk profile includes a categorical readmission risk level determined for the patient.

19. The system of claim 14, wherein determining the readmission risk profile comprises:

predicting, for the patient, a plurality of risk levels including a respective risk level of each of a plurality of readmission risk factors; and determining the readmission risk level based on the plurality of risk levels.

20. The system of claim 14, wherein the operation further comprises parsing the patient record by:

tokenizing text in the patient record and normalizing the tokenized text;

converting the tokenized text into an object that is represented numerically using at least one of one-hot encodings or word embedding vectors; and processing the object using a natural language processing algorithm.

* * * * *